US012186236B2

(12) United States Patent
Chen et al.

(10) Patent No.: US 12,186,236 B2
(45) Date of Patent: Jan. 7, 2025

(54) ADJUSTABLE STIFFENER FOR SURGICAL INSTRUMENTS

(71) Applicant: Alcon Inc., Fribourg (CH)

(72) Inventors: Bill Chen, Irvine, CA (US); James Y. Chon, Irvine, CA (US); Russell Finlay, Keller, TX (US); Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 344 days.

(21) Appl. No.: 17/807,778

(22) Filed: Jun. 20, 2022

(65) Prior Publication Data

US 2023/0064225 A1 Mar. 2, 2023

Related U.S. Application Data

(60) Provisional application No. 63/237,361, filed on Aug. 26, 2021.

(51) Int. Cl.
*A61F 9/007* (2006.01)
*A61B 17/00* (2006.01)

(52) U.S. Cl.
CPC .............. *A61F 9/00736* (2013.01); *A61B 2017/00336* (2013.01)

(58) Field of Classification Search
CPC .......... A61F 9/00736; A61B 2017/00336
See application file for complete search history.

(56) References Cited

U.S. PATENT DOCUMENTS

| 3,805,787 A | 4/1974 | Banko |
| 4,030,567 A | 6/1977 | Kondo |
| 5,019,035 A | 5/1991 | Missirlian |
| 5,190,050 A | 3/1993 | Nitzsche |
| 5,217,465 A | 6/1993 | Steppe |
| 5,370,658 A | 12/1994 | Scheller |
| 5,396,880 A | 3/1995 | Kagan et al. |
| 6,312,402 B1 | 11/2001 | Hansmann |
| 6,575,989 B1 | 6/2003 | Scheller |
| 6,749,601 B2 | 6/2004 | Chin |
| 6,908,476 B2 | 6/2005 | Jud |
| 6,945,984 B2 | 9/2005 | Arumi |
| 7,207,980 B2 | 4/2007 | Christian |
| 7,338,494 B2 | 3/2008 | Ryan |
| 7,909,816 B2 | 3/2011 | Buzawa |
| 8,038,692 B2 | 10/2011 | Valencia |

(Continued)

FOREIGN PATENT DOCUMENTS

| CN | 202426711 U | 9/2012 |
| CN | 207755450 U | 8/2018 |

(Continued)

*Primary Examiner* — Julian W Woo

(57) ABSTRACT

A surgical instrument includes a base unit, a probe, a stiffener, and an actuation mechanism. The stiffener is formed of a hollow tubular member substantially surrounding at least a portion of a length of the probe. The actuation mechanism is configured to actuate the stiffener along the length of the probe and adjust the stiffness of the probe, thus providing a user better control of the surgical instrument. The actuation mechanism includes a stiffener biasing device configured to apply a first biasing force against the stiffener in the distal direction and, in some embodiments, a control member configured to lock the stiffener in a position along the length of the probe.

16 Claims, 14 Drawing Sheets

(56) References Cited

U.S. PATENT DOCUMENTS

| | | | |
|---|---|---|---|
| 8,187,293 B2 | 5/2012 | Kirchhevel | |
| 8,202,277 B2 | 6/2012 | Ryan | |
| 8,216,246 B2 * | 7/2012 | Luloh | A61F 9/00763 |
| | | | 606/107 |
| 8,308,737 B2 | 11/2012 | Ryan | |
| 8,845,666 B2 | 9/2014 | Underwood | |
| 8,894,636 B2 | 11/2014 | Gille et al. | |
| 9,060,841 B2 | 6/2015 | Mccawley | |
| 9,138,346 B2 | 9/2015 | Scheller | |
| 9,370,447 B2 | 6/2016 | Mansour | |
| 9,585,788 B2 | 3/2017 | Underwood | |
| 9,757,274 B2 | 9/2017 | Scheller et al. | |
| 9,775,943 B2 | 10/2017 | Scheller | |
| 9,795,505 B2 | 10/2017 | Yu et al. | |
| 9,925,326 B2 | 3/2018 | Scheller | |
| 9,931,244 B2 | 4/2018 | Ryan | |
| 9,949,876 B2 | 4/2018 | Mansour | |
| 10,045,883 B2 | 8/2018 | Egli | |
| 10,085,883 B2 | 10/2018 | Auld | |
| 10,179,007 B2 * | 1/2019 | Peterson | A61F 9/007 |
| 10,285,583 B2 | 5/2019 | Parto | |
| 10,376,315 B2 | 8/2019 | Scheller et al. | |
| 10,391,232 B2 | 8/2019 | Scheller et al. | |
| 10,413,445 B2 | 9/2019 | Scheller et al. | |
| 10,413,446 B2 | 9/2019 | Bouch et al. | |
| 10,617,560 B2 | 4/2020 | Ryan | |
| 10,639,197 B2 | 5/2020 | Lopez | |
| 10,675,181 B2 | 6/2020 | Murakami | |
| 10,828,192 B2 | 11/2020 | Scheller et al. | |
| 10,898,373 B2 | 1/2021 | Ryan | |
| 10,945,882 B2 | 3/2021 | Ryan | |
| 11,020,270 B1 | 6/2021 | Peyman | |
| 11,278,449 B2 | 3/2022 | Ryan | |
| 2003/0195539 A1 | 10/2003 | Attinger | |
| 2005/0033309 A1 | 2/2005 | Ryan | |
| 2005/0209618 A1 | 9/2005 | Auld | |
| 2007/0099149 A1 | 5/2007 | Levy et al. | |
| 2007/0106300 A1 | 5/2007 | Auld | |
| 2007/0255196 A1 | 11/2007 | Wuchinich | |
| 2008/0195135 A1 | 8/2008 | Attinger | |
| 2008/0255526 A1 | 10/2008 | Bosse et al. | |
| 2009/0093800 A1 | 4/2009 | Auld | |
| 2009/0131870 A1 | 5/2009 | Fiser | |
| 2010/0063359 A1 | 3/2010 | Okoniewski | |
| 2010/0228226 A1 | 9/2010 | Nielsen | |
| 2012/0116361 A1 | 5/2012 | Hanlon et al. | |
| 2013/0090531 A1 | 4/2013 | Ryan | |
| 2013/0090635 A1 | 4/2013 | Mansour | |
| 2013/0197488 A1 | 8/2013 | Scheller et al. | |
| 2013/0281817 A1 | 10/2013 | Schaller | |
| 2014/0121469 A1 | 5/2014 | Meckel et al. | |
| 2014/0128896 A1 | 5/2014 | Ryan | |
| 2015/0231687 A1 | 8/2015 | Ookubo et al. | |
| 2016/0022256 A1 | 1/2016 | Peterson | |
| 2017/0215855 A1 | 8/2017 | Nunan | |
| 2017/0333251 A1 | 11/2017 | Scheller et al. | |
| 2018/0214307 A1 | 8/2018 | Ryan | |
| 2018/0228651 A1 | 8/2018 | Mansour | |
| 2018/0250164 A1 | 9/2018 | Ryan | |
| 2018/0360660 A1 | 12/2018 | Lopez | |
| 2019/0059936 A1 | 2/2019 | Ryan | |
| 2019/0269556 A1 | 9/2019 | Meckel | |
| 2019/0282322 A1 | 9/2019 | Mirsepassi | |
| 2020/0163717 A1 | 5/2020 | Hartkopf-ceylan | |
| 2020/0197217 A1 | 6/2020 | Ryan | |
| 2021/0177652 A1 | 6/2021 | Chen et al. | |
| 2021/0177653 A1 | 6/2021 | Hallen | |
| 2021/0244567 A1 | 8/2021 | Ryan | |
| 2021/0251805 A1 | 8/2021 | Ryan | |
| 2021/0290438 A1 | 9/2021 | Hallen | |
| 2022/0031509 A1 | 2/2022 | Tazawa | |
| 2022/0192706 A1 | 6/2022 | Grueebler et al. | |

FOREIGN PATENT DOCUMENTS

| | | |
|---|---|---|
| DE | 651436 C | 10/1937 |
| EP | 1782781 A1 | 5/2007 |
| EP | 1955684 A1 | 8/2008 |
| EP | 2760400 B1 | 1/2018 |
| EP | 3319564 B1 | 11/2019 |
| EP | B191161 B1 | 1/2020 |
| EP | 3656332 A1 | 5/2020 |
| EP | 3352682 B1 | 7/2020 |
| EP | 3332756 B1 | 8/2020 |
| GB | 1448129 A | 9/1976 |
| JP | 2009072221 A | 4/2009 |
| JP | 2020044289 A | 3/2020 |
| JP | 2022040303 A | 3/2022 |
| WO | 0119255 A1 | 3/2001 |
| WO | 2010064670 A1 | 6/2010 |
| WO | 2013133712 A1 | 9/2013 |
| WO | 2016019160 A1 | 2/2016 |
| WO | 2017053832 A1 | 3/2017 |
| WO | 2017075514 A1 | 5/2017 |

* cited by examiner

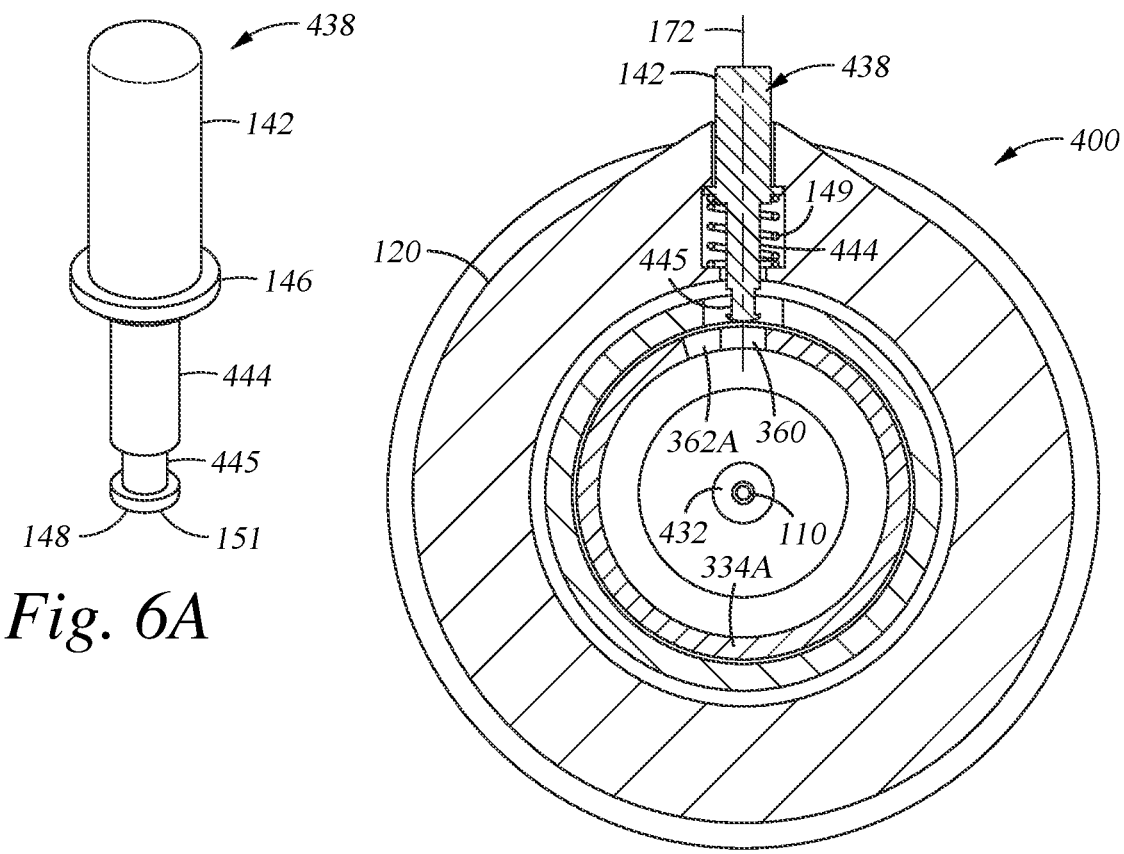
Fig. 6A
Fig. 6B
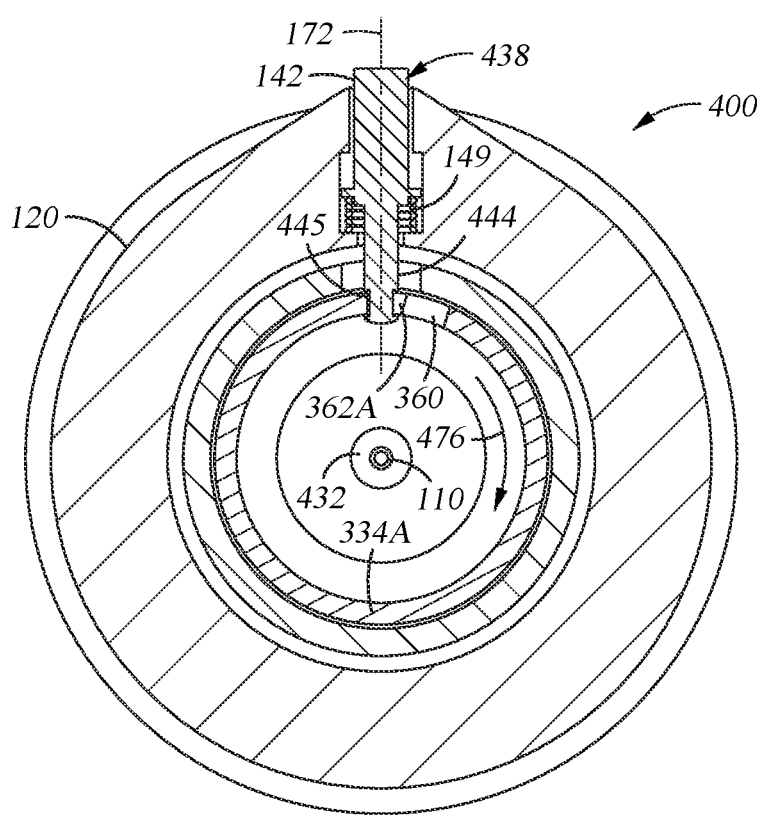
Fig. 6C

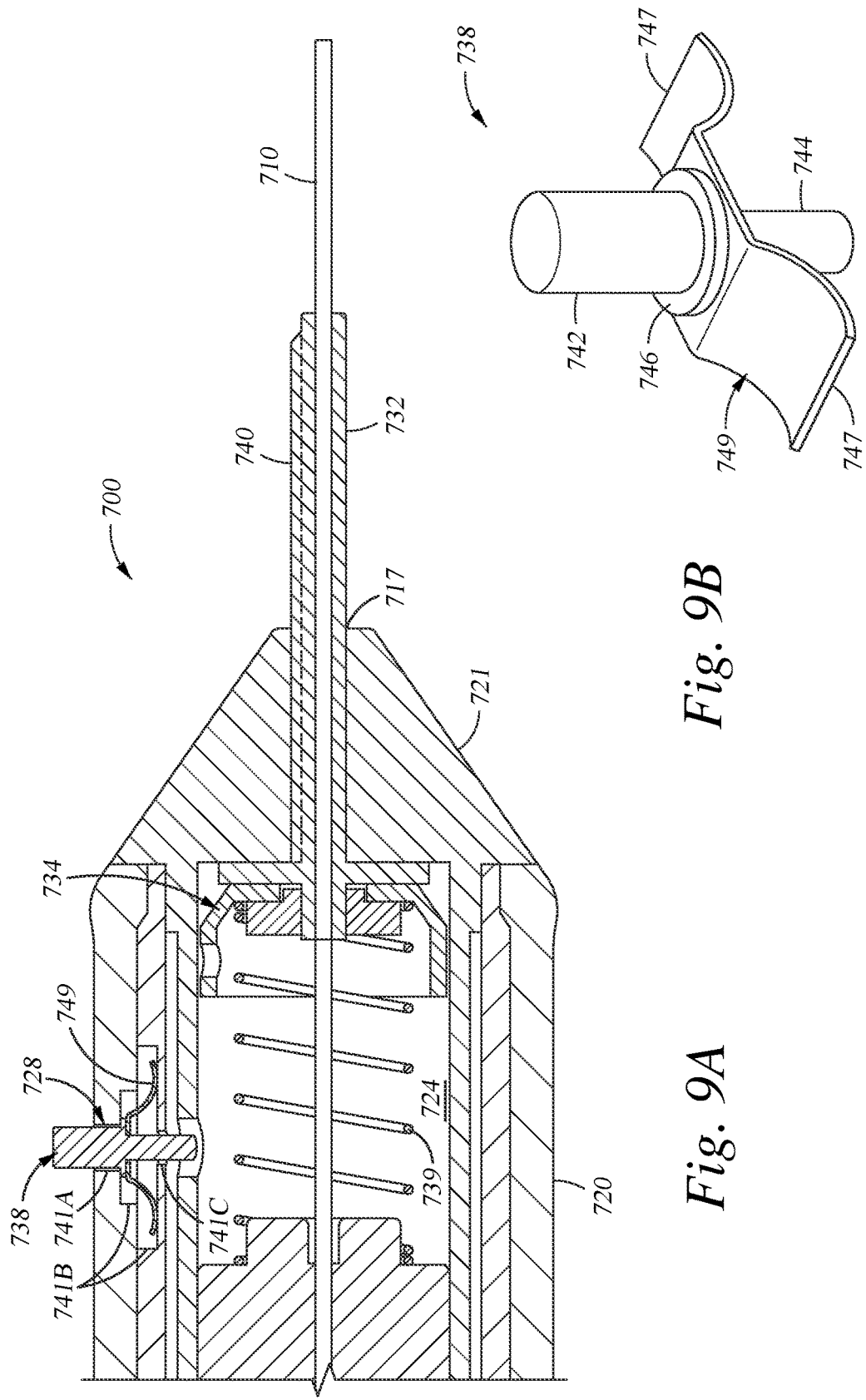

ADJUSTABLE STIFFENER FOR SURGICAL INSTRUMENTS

PRIORITY CLAIM

This application claims the benefit of priority of U.S. Provisional Patent Application Ser. No. 63/237,361 titled "Adjustable Stiffener for Surgical Instruments," filed on Aug. 26, 2021, whose inventors are Bill Chen, James Y. Chon, Russell Finlay, and Paul Hallen, which is hereby incorporated by reference in its entirety as though fully and completely set forth herein.

BACKGROUND

Field

Embodiments of the present disclosure generally relate to small-gauge instrumentation for surgical procedures, and more particularly, small-gauge instrumentation for ophthalmic surgical procedures.

Description of the Related Art

Continuous efforts to minimize the invasiveness of surgical procedures, such as ophthalmic surgical procedures, have led to the development of small-gauge surgical instrumentation, which are referred to as microsurgical instruments, for microincision techniques. Small gauge vitrectomy, also known as minimally invasive vitreous surgery (MIVS), is a classic example of one such type of surgical procedure utilizing small-gauge instrumentation. Examples of common ocular conditions that may be treated by minimally invasive vitreous surgery include retinal detachment, macular holes, premacular fibrosis, and vitreous hemorrhages. The benefits associated with modern MIVS as compared to more invasive vitrectomies include access to greater pathology, greater fluidic stability, increased patient comfort, less conjunctival scarring, less postoperative inflammation, and earlier visual recovery, among others. Accordingly, indications for MIVS and other microincision techniques have expanded in recent years.

Despite the aforementioned benefits of microincision techniques and their widespread acceptance, there remain numerous challenges with the utilization of small-gauge surgical instruments, particularly in the field of ophthalmology. One commonly noted concern among surgeons is instrument rigidity. The smaller diameter of these microincision instruments, such as vitrectomy probes, causes decreased stiffness thereof, making it difficult for surgeons to control the instruments during certain ocular surgical procedures. With small-gauge ophthalmic surgical instruments, for example, the instrument tips can move in unintended directions at the extreme limits of the eye, thus making delicate procedures such as the peeling of membranes from the retinal surface extremely difficult.

Accordingly, what is needed in the art are improved methods and apparatus for minimally-invasive ophthalmic surgical procedures.

SUMMARY

The present disclosure generally relates to surgical instruments, and more particularly, microsurgical instruments for ophthalmic surgical procedures.

In certain embodiments, a surgical instrument is provided that includes a base unit and a probe. The base unit is configured to be held by a user. The probe is disposed through a base unit opening in a distal end of the base unit and has a length parallel to a probe longitudinal axis thereof. The surgical instrument further includes a stiffener extending through the base unit opening in the base unit and an actuation mechanism configured to actuate the stiffener along the length of the probe in a distal direction. The stiffener is formed of a hollow tubular member that surrounds at least a portion of the probe and is slidably coupled thereto. The actuation mechanism includes a stiffener biasing device configured to apply a first biasing force against the stiffener in the distal direction. In some embodiments, the actuation mechanism further includes a control member configured to lock the stiffener in position.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 6A illustrates a perspective view of another exemplary control member, according to certain embodiments of the present disclosure.

FIG. 6B-6C illustrate a schematic front cross-sectional view of another exemplary instrument, according to certain embodiments of the present disclosure.

FIG. 9A illustrates a cross-sectional view of another exemplary instrument, according to certain embodiments of the present disclosure.

FIG. 9B illustrates a perspective view of a control member of the instrument of FIG. 9A, according to certain embodiments of the present disclosure.

Figure 1A:
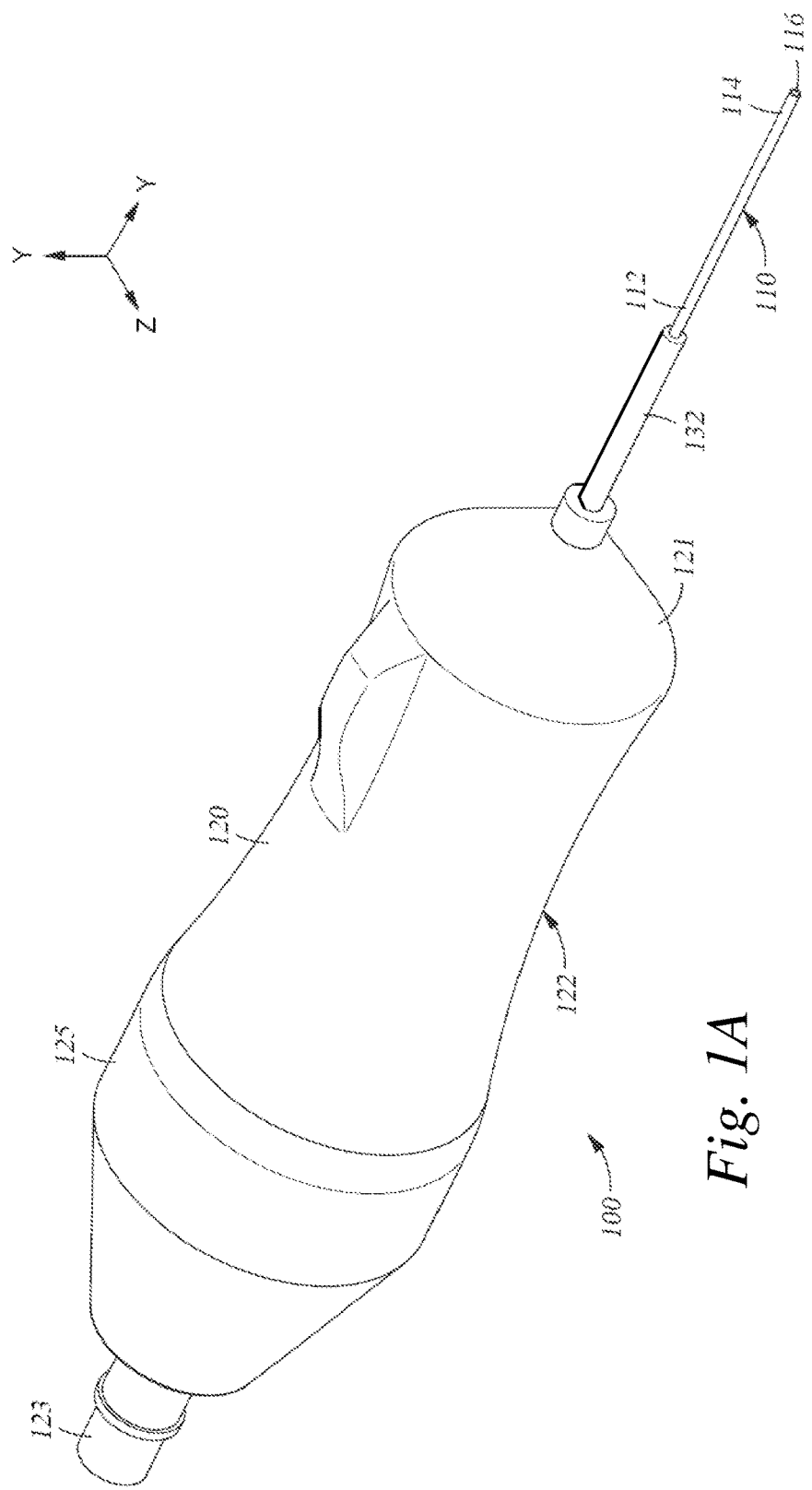
FIG. 1A illustrates a perspective view of a vitrectomy probe with a dynamically adjustable stiffening sleeve, according to certain embodiments of the present disclosure.

To facilitate understanding, identical reference numerals have been used, where possible, to designate identical elements that are common to the figures. It is contemplated that elements and features of certain embodiments may be beneficially incorporated in other embodiments without further recitation.

DETAILED DESCRIPTION

In the following description, details are set forth by way of example to facilitate an understanding of the disclosed subject matter. It should be apparent to a person of ordinary skill in the art, however, that the disclosed implementations are exemplary and not exhaustive of all possible implementations. Thus, it should be understood that reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Note that, as described herein, a distal end, segment, or portion of a component refers to the end, segment, or portion that is closer to a patient's body during use thereof. On the other hand, a proximal end, segment, or portion of the component refers to the end, segment, or portion that is distanced further away from the patient's body. An intermediate segment or portion of a component refers to the segment or portion that is positioned between the distal segment or portion and the proximal end or portion.

As used herein, the term "about" may refer to a +/−10% variation from the nominal value. It is to be understood that such a variation can be included in any value provided herein.

The present disclosure generally relates to surgical instruments, such as microsurgical instruments having variable stiffness, and more particularly, microsurgical instruments having variable stiffness for ophthalmic surgical procedures (e.g., vitrectomy probes, illuminator probes, etc.) In certain embodiments, a microsurgical instrument includes a probe and a stiffener. The stiffener may be formed of a hollow tubular member substantially surrounding at least a portion of a length of the probe. Actuation of the stiffener along the length of the probe adjusts the stiffness of the probe, thus providing a user better control of the microsurgical instrument. The stiffener may include a de-coupler and, in some embodiments, may be locked or maintained at different positions along the length of the probe through the interaction of the de-coupler and a control member. In some embodiments, the de-coupler may de-couple the stiffener from a biasing spring without a control member. In some embodiments, using a stiffener locking mechanism may allow the user to set and "lock-in" the stiffness of the microsurgical instrument to a desired level.

FIG. 1A illustrates a perspective view of a vitrectomy probe 100 with a dynamically adjustable stiffening sleeve 132, according to certain embodiments. As depicted in FIG. 1A, the instrument 100 comprises a probe 110 or needle (referred to hereinafter as a "probe") and a base unit 120. The probe 110 includes a proximal portion 112 and a distal portion 114 which terminates distally at a distal end 116. In some embodiments, the proximal portion 112 extends through a substantial portion of an interior chamber (e.g., an interior chamber 124 in FIGS. 2, 4A, and 4B) of the base unit 120.

Figure 3A:
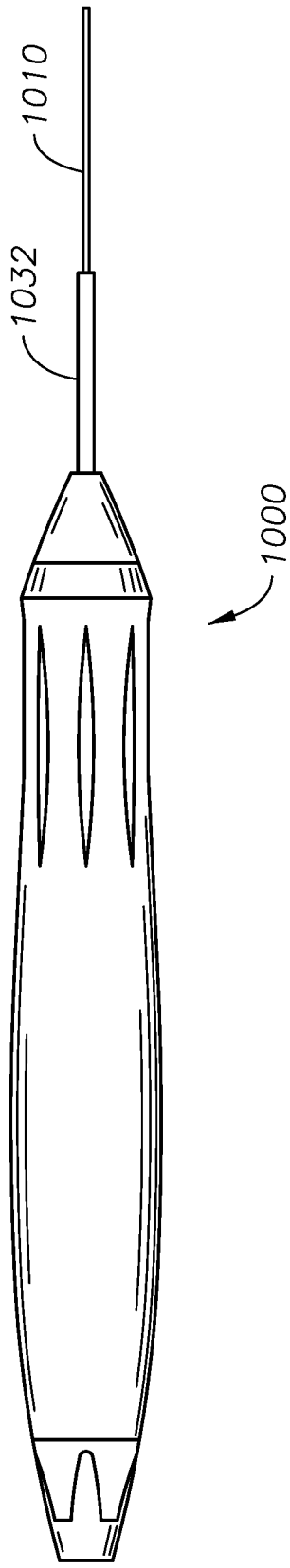
FIG. 3A illustrates a perspective view of an illuminator probe with a dynamically adjustable stiffening sleeve, according to certain embodiments of the present disclosure.
Figure 3B:
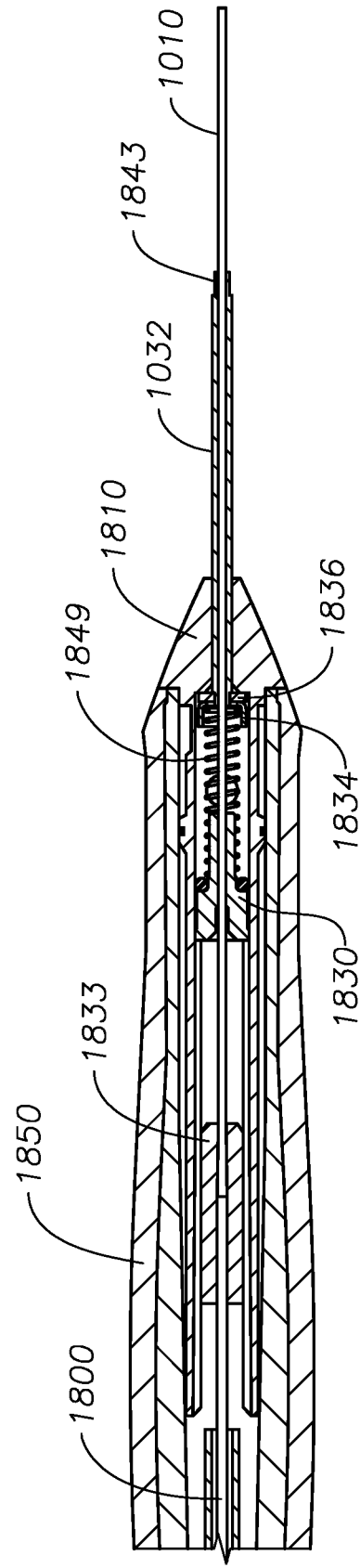
FIG. 3B illustrates a schematic cross-sectional side view of the illuminator probe of FIG. 3A, according to certain embodiments of the present disclosure.

In one example, the probe 110 is an elongated cutting member of a vitrectomy probe. For example, the probe 110, which may be aspirating or non-aspirating, may be inserted into a cannula for performance of vitreous surgery. The probe 110 may comprise a hollow tube having, e.g., a diameter less than about 20 gauge. For example, the probe 110 has a diameter less than about 23 gauge, such as a diameter less than about 25 gauge. In certain embodiments, the probe 110 has a diameter of approximately 27 gauge. In further examples, the probe 110 may include an illumination device (e.g., as seen in FIGS. 3A-3B), a laser guide, a suction device, forceps, scissors, retractors, or other suitable devices disposed therein or coupled thereto.

Generally, the probe 110 is formed of a material suitable for minimally invasive surgical procedures, such as vitreo-retinal surgeries that involve removal of the vitreous in the eye, or other surgical procedures. For example, the probe 110 is formed of surgical grade stainless steel, aluminum, or titanium.

The probe 110 is partially and longitudinally disposed through a distal end 121 of the base unit 120 adjacent the proximal portion 112 of the probe 110 and may be directly or indirectly attached thereto within the interior chamber 124 of the base unit 120. In certain embodiments, the base unit 120 is a handpiece having an outer surface 122 configured to be held by a user, such as a surgeon. For example, the base unit 120 may be contoured to substantially fit the hand of the user. In some embodiments, the outer surface 122 may be textured or have one or more gripping features formed thereon, such as one or more grooves and/or ridges.

In certain embodiments, the base unit 120 may house at least a portion of a drive mechanism operable to reciprocate the probe 110 within and relative to the base unit 120. In one example, the drive mechanism may be a pneumatic drive mechanism including a diaphragm. The base unit 120 may further provide one or more ports 123 at a proximal end 125 thereof for one or more supply lines to be routed into the interior chamber 124. For example, the one or more ports 123 may provide a connection between the base unit 120 and a vacuum source for aspiration. In another example, the one or more ports 123 provide a connection to a pneumatic, hydraulic, or electrical power source to operate the drive mechanism, an illumination device, a laser, or other suitable device within or coupled to the base unit 120.

The instrument 100 further includes a stiffener 132 slidably coupled to and substantially surrounding at least a portion of the probe 110. The stiffener 132 is adjustable relative to the probe 110, enabling a user to position the stiffener 132 (e.g., a distal end 131 of the stiffener 132) at different points along a length L of the probe 110 exterior to the base unit 120.

In some embodiments the stiffener 132 is generally a cylindrical and hollow tube substantially surrounding the probe 110 at or near the proximal portion 112. Similar to the probe 110, the stiffener 132 is formed of a material suitable for minimally invasive surgical procedures, such as vitreoretinal surgeries and other surgical procedures. In some embodiments, the stiffener 132 is formed of a metallic material, such as surgical grade stainless steel, aluminum, or titanium. In other embodiments, the stiffener 132 is formed of a composite material, such as a polymer composite material or a ceramic composite material.

Figure 2:
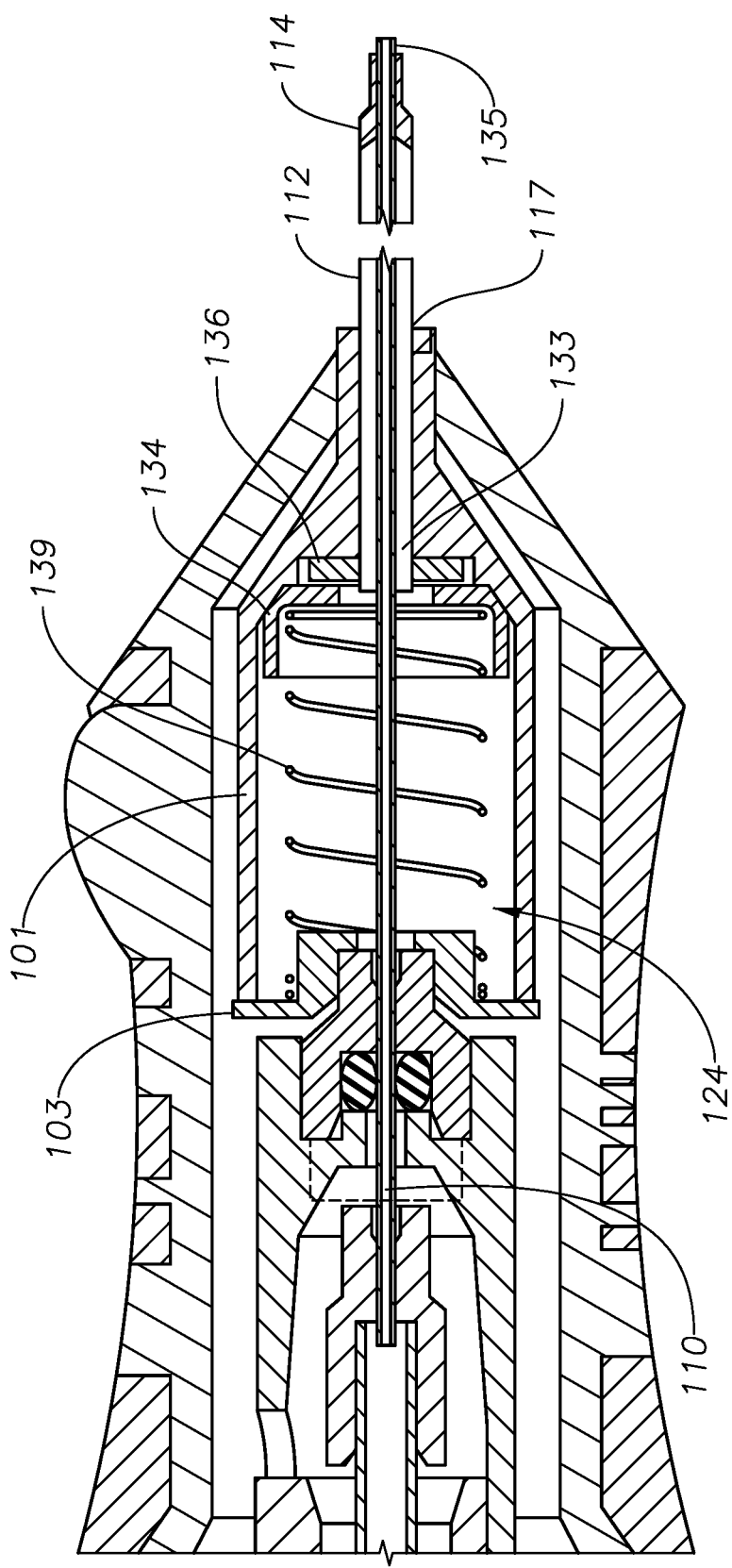
FIG. 2 illustrates a schematic cross-sectional side view of the vitrectomy probe of FIG. 1A, according to certain embodiments of the present disclosure.
Figure 4A:
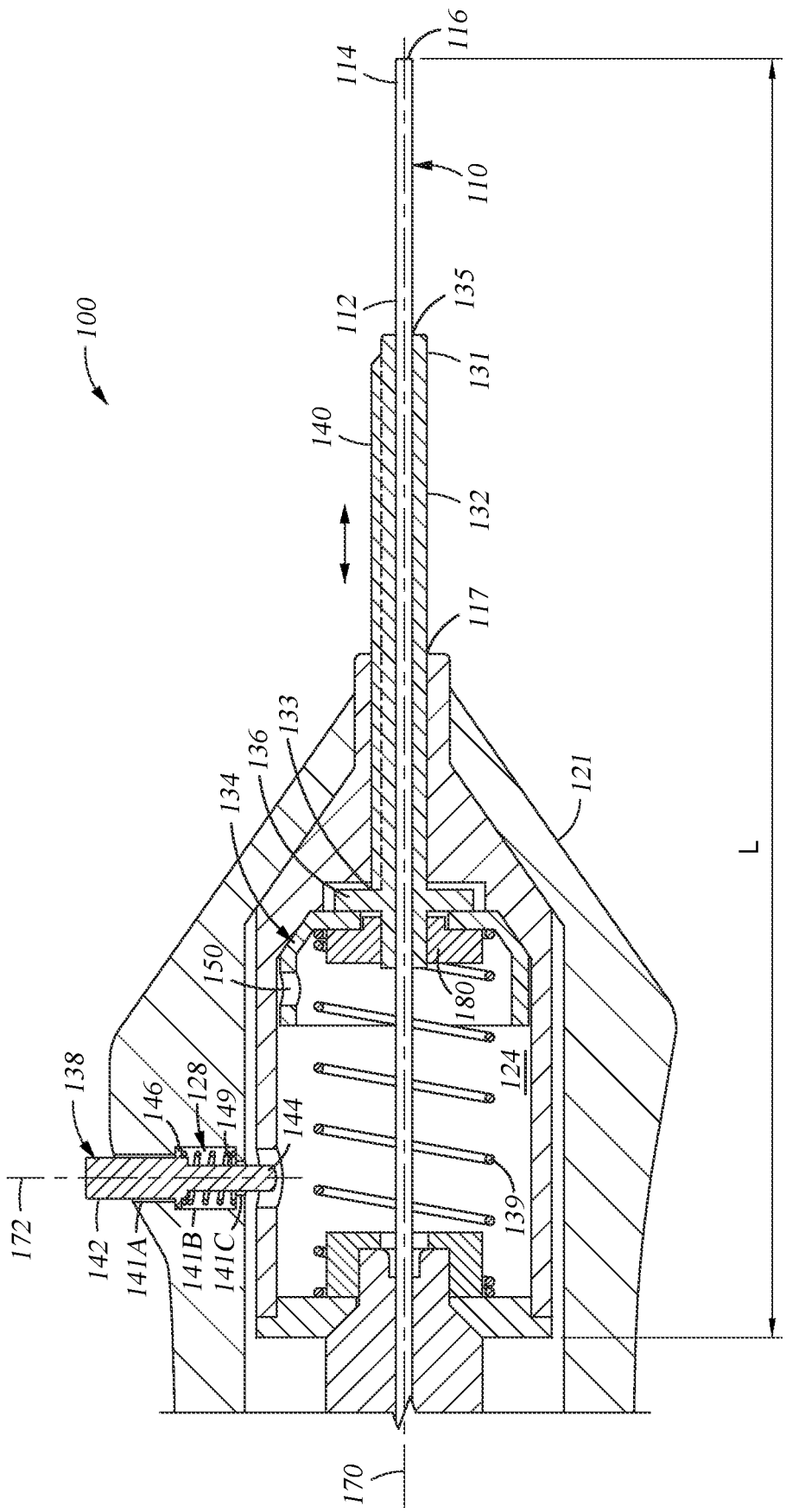
FIGS. 4A-4B illustrates schematic cross-sectional side views of the vitrectomy probe of FIG. 1B, according to certain embodiments of the present disclosure.
Figure 4B:
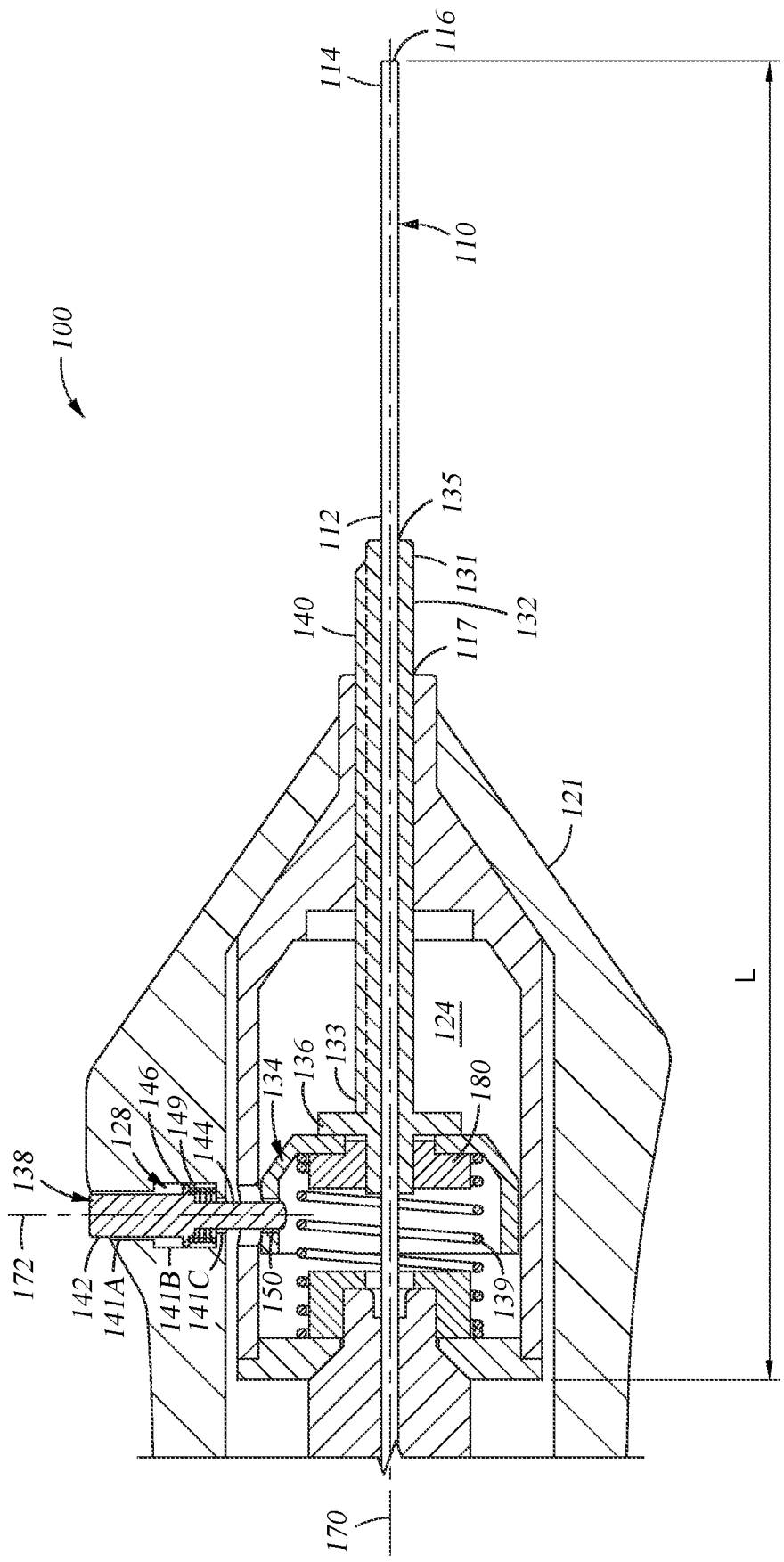

As seen in FIG. 2 and FIGS. 4A-4B, an inner cavity 135 of the stiffener 132 is sized to accommodate an outer diameter of the probe 110 while also permitting the stiffener 132 to be readily moved along the probe 110. Thus, an inner diameter or width of the stiffener 132 is greater than the outer diameter of the probe 110 and enables a sliding fit. In one embodiment, a radial clearance between the stiffener 132 and the probe 110 is between about 0.00020 inches and about 0.00060 inches, such as between about 0.00025 inches and about 0.00050 inches. For example, the radial clearance between the stiffener 132 and the probe 110 is between about 0.00030 inches and about 0.00040 inches, such as about 0.00035 inches. Further, the inner dimensions of the stiffener 132 may be uniform from the distal end 131 to the proximal end 133 to enable uniform stabilization of the probe 110 throughout the inner cavity of the stiffener 132.

Along with the probe 110, the stiffener 132 is disposed through the base unit opening 117 of the distal end 121 of the base unit 120 and has a proximal end 133 disposed in the interior chamber 124 of the base unit 120. As shown, the stiffener 132 includes an annular flange (e.g., flange 136) disposed at its proximal end 133 within the interior chamber 124. In other embodiments, the flange 136 is disposed more axially along a length of the stiffener 132. The flange 136 is configured to prevent the stiffener 132 from completely sliding through the base unit opening 117 and out of the base unit 120. Thus, the flange 136 acts as an anchor in one capacity. The flange 136 provides a coupling surface between the stiffener 132 and a de-coupler 134, which is further coupled to a stiffener biasing device 139 (e.g., a spring such as a compression spring). In some embodiments, the stiffener 132 may include a reduced diameter nose 143. The reduced diameter nose 143 may be able to extend further into a cannula in an eye of a patient.

The stiffener biasing device 139 applies a biasing force against the de-coupler 134 and thus the stiffener 132 in a distal direction (e.g., towards the distal end 121) to bias the stiffener 132 towards a protracted position. Thus, without an application of a force in an opposite, proximal direction (e.g., towards the proximal end 125 in FIG. 1B), the stiffener 132 is constantly disposed in the protracted position. During use, the probe 110 may be inserted into an insertion cannula with a hub (e.g., including a valve), at a desired depth. Upon a distal end 131 of the stiffener 132 reaching the hub of the insertion cannula, the user may further press the instrument 100 towards the hub to drive the probe 110 deeper therein. Application of a force against the hub greater than that of the force provided by the stiffener biasing device 139 will cause the stiffener 132 to retract into the base unit 120 (shown in FIG. 4B), allowing a greater portion of the probe 110 to enter the eye.

In certain embodiments, the stiffener 132 is sized to possess an axial length sufficient to provide a desired rigidity and stability to the probe 110 while having a portion thereof still remaining in the interior chamber 124 when the stiffener 132 is in the protracted position. For example, the stiffener 132 may have an axial length between about 0.25 inches and about 1.75 inches, such as between about 0.30 inches and about 1.50 inches. For example, the stiffener 132 may have an axial length between about 0.50 inches and about 1.25 inches.

In certain embodiments, the stiffener 132 has a uniform outer diameter from the distal end 131 to the proximal end 133. Having a uniform outer diameter enables a substantial length of the stiffener 132 to be reciprocated through the base unit opening 117 without forming an air gap therebetween. However, other shapes and morphologies of the stiffener 132 are also contemplated. For example, in some embodiments, the stiffener 132 comprises a square, rectangular, or polygonal tube. In further embodiments, the stiffener 132 may have a non-uniform outer diameter. For example, the stiffener 132 may have an outer diameter having one or more dimensions following a step-wise or gradual delta.

In some embodiments, the actuation mechanism may include a biasing device 139, a de-coupler 134, and an annular flange 136 integral with or affixed to the stiffener 132 such that the biasing device is configured to apply a biasing force, through the de-coupler 134, against the annular flange 136 of the stiffener 132 in the distal direction. In some embodiments, the de-coupler 134 and the stiffener 132 are separate components that are biased toward each other by, for example, biasing device 139 (such as a spring). The de-coupler 134 may contact annular flange 136 due to the biasing device 139 biasing the de-coupler 134 toward the annular flange 136 and/or due to external forces on the stiffener 132 pushing the annular flange 136 (which may be integral with or attached to the stiffener 132) toward the de-coupler 134. In some embodiments, the de-coupler 134 and annular flange 136 may be otherwise not attached to each other to allow relative movement between the de-coupler 134 and annular flange 136.

Figure 1B:
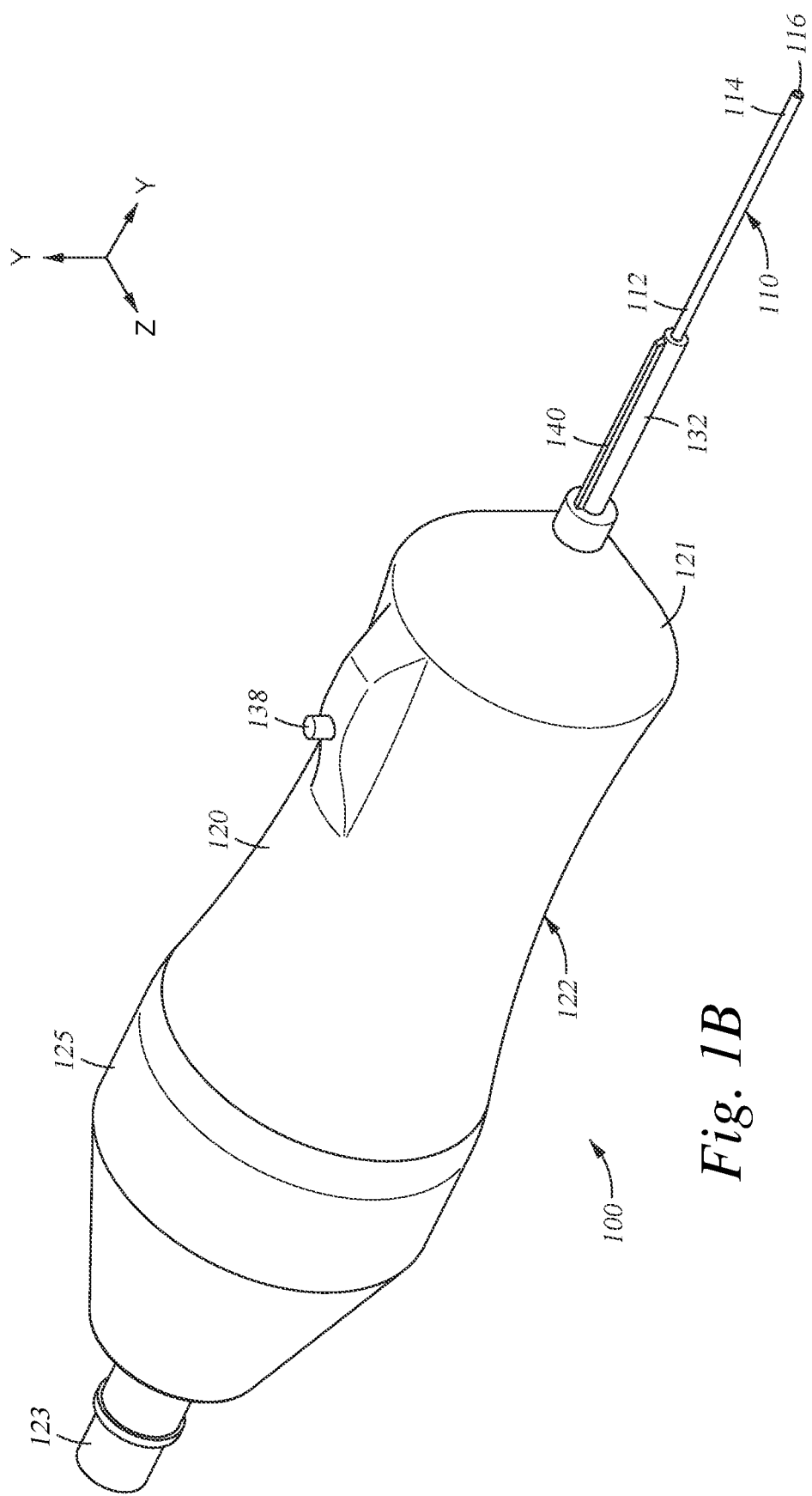
FIG. 1B illustrates a perspective view of a vitrectomy probe with a dynamically adjustable stiffening sleeve and a control member, according to certain embodiments of the present disclosure.

FIG. 1B illustrates a perspective view of a vitrectomy probe with a dynamically adjustable stiffening sleeve and a control member 138. In certain embodiments, the position of the stiffener 132 is locked in place using the control member 138 as described below in relation to FIGS. 4A-4C. Accordingly, a user may selectively adjust the level of stiffness of the probe 110 by re-positioning the stiffener 132 relative to the distal end 116, thereby manipulating the amount of support provided to the probe 110 and stabilizing the instrument 100 during use thereof.

In some embodiments, the stiffener 132 includes a keying feature 140 configured to operatively engage a base unit opening (e.g., a base unit opening 117 in FIG. 4A) in the distal end 121 of the base unit 120 to prevent rotation of the stiffener 132 as further described in FIG. 4A. As shown, the keying feature 140 is a protrusion of the stiffener 132 with a rectangular-shaped cross-section but may be other shapes in other embodiments, such as a semi-circle or triangle. Note that although FIG. 1B shows a keying feature 140, in certain embodiments (for example, as seen in FIG. 1A), a keying feature 140 is not used.

FIG. 3A illustrates a perspective view of an illuminator probe 1000 with a dynamically adjustable stiffening sleeve 1032, according to certain embodiments of the present disclosure. FIG. 3B illustrates a schematic cross-sectional side view of the illuminator probe 1000 of FIG. 3A. Illuminator probe 1000 may comprise a cannula 1010 surrounding an optical fiber 1800 that guides light, for example, into the interior of an eye. Dynamically adjustable stiffening sleeve 1032 may include an annular flange 1836 that engages a control member biasing device (e.g., spring 1849). As stiffening sleeve 1032 is biased toward a handle portion 1850 (e.g., as it encounters opposing structure such as a trocar cannula), stiffening sleeve 1032 may enter nose 1810 and an interior of the handle portion 1850. In some embodiments, the stiffening sleeve 1032 may include a reduced diameter nose 1843. The reduced diameter nose may be able to extend further into a cannula in an eye of a patient. In some embodiments, the dynamically adjustable stiffening sleeve 1032 may include a biasing device 1849, a de-coupler 1834, and an annular flange 1836 integral with or affixed to the stiffener 1032 such that the biasing device is configured to apply a biasing force, through the de-coupler 1834, against the annular flange 1836 of the stiffener 1032 in the distal direction. In some embodiments, the de-coupler 1834 and the stiffener 1032 are separate components that are biased toward each other by, for example, biasing device 1849 (such as a spring). The de-coupler 1834 may contact annular flange 1836 due to the biasing device 1849 biasing the de-coupler 1834 toward the annular flange 1836 and/or due to external forces on the stiffener 1032 pushing the annular flange 1836 (which may be integral with or attached to the stiffener 1032) toward the de-coupler 1834. In some embodiments, the de-coupler 1834 and annular flange 1836 may be otherwise not attached to each other to allow relative movement between the de-coupler 1834 and annular flange 1836.

In some embodiments, spring 1849 may bias against the de-coupler 1834 and annular flange 1836 to restore the stiffening sleeve 1032 to its extended position as the illuminator probe 1000 is withdrawn (and the stiffening sleeve is no longer biased against the opposing structure). In some embodiments, the spring may be fixed against plug 1830. In some embodiments, spring 1849 may not be affixed to de-coupler 1834 or plug 1830. In some embodiments, spring 1849 may be affixed to de-coupler 1834 and/or plug 1830. As further seen in FIG. 3B, in some embodiments a coupler 1833 may couple optical fibers (one optical fiber 1800 extending outside of the handle 1850 and one optical fiber extending to the tip). In some embodiments, the optical fiber may be continuous from the exterior of the handle through to the tip (without using a coupler 1833).

FIGS. 4A and 4B illustrate schematic cross-sectional views of the instrument 100 with the stiffener 132 positioned at different points along a length L of the probe 110. Therefore, FIGS. 4A and 4B are herein described together with FIG. 1B for clarity. When the stiffener 132 is positioned at different points along the length L, the keying feature 140 operatively engages the base unit opening 117 and prevents the stiffener 132 from rotating. This beneficially ensures the opening of the de-coupler 134 (referred to as de-coupler opening) does not rotate. A dashed line is shown between a cylindrical body of the stiffener and the keying feature 140 in FIGS. 4A and 4B, and later figures including the stiffener 132, to emphasize that the keying feature 140 protrudes from the rest of the stiffener 132.

In some embodiments, the stiffener biasing device 139 applies a biasing force against the de-coupler 134 and thus the stiffener 132 in a distal direction (e.g., towards the distal end 121) to bias the stiffener 132 towards a protracted position along the length L of the probe 110, as shown in FIG. 4A. During use, the probe 110 may be inserted into an insertion cannula with a hub (e.g., including a valve), at a desired depth along the length L selected by the user. Upon a distal end 131 of the stiffener 132 reaching the hub of the insertion cannula, the user may further press the instrument 100 towards the hub to drive the probe 110 deeper therein. Application of a force against the hub greater than that of the force provided by the stiffener biasing device 139 will cause the stiffener 132 to retract into the base unit 120 (shown in FIG. 4B), allowing a greater portion of the probe 110 to enter the eye. Once retracted, the stiffener 132 can be locked in the retracted position by the control member 138.

As shown in FIG. 4B, the position of the stiffener 132 can be locked or maintained through the interaction of the control member 138 and the de-coupler 134. For example, a surgeon may press the control member 138 radially-inward towards the de-coupler 134, thereby causing the control member 138 and the de-coupler 134 to engage for locking the stiffener 132 in position. More specifically, the control member 138 operationally engages the de-coupler 134 through an opening 150 in the de-coupler 134. The control member 138 may be a button, knob, switch, toggle, or any other suitable device capable of being actuated by a user. As shown, the de-coupler opening 150 is a through hole.

As depicted in FIGS. 4A and 4B, the control member 138 includes a head 142, a protrusion (e.g., a shaft 144), and a flange 146, wherein the head 142 and the shaft 144 are disposed at opposite ends of the control member 138 and the flange 146 is in between. The control member 138 is partially disposed within a cutout 128 (e.g., a channel or an opening) formed in the base unit 120. The cutout 128 includes multiple-sized passageways 141 configured to accommodate the features of the control member 138. For example, the head 142 is disposed in a first passageway 141A, the flange 146 is disposed in a second passageway 141B, and the shaft 144 is at least partially disposed in a third passageway 141C. The flange 146 operatively engages the second passageway 141B to guide the control member 138 through the cutout 128 and ensure the control member 138 remains coupled to the base unit 120. The cutout 128 runs substantially perpendicular to a longitudinal axis 170 of the probe 110 (referred to as a probe longitudinal axis) and enables bidirectional pushing of the control member 138 along a perpendicular axis 172 thereof. The perpendicular axis 172 may be referred to as a longitudinal axis of and with respect to the control member (e.g., a control member longitudinal axis) that is different from the probe longitudinal axis of the probe 110.

As shown, a control member biasing device 149 (e.g., a spring) is disposed in the second passageway 141B to bias the control member 138 in a radially outward direction along the perpendicular axis 172. The control member biasing device 149 applies a control member biasing force against the control member 138 in a direction substantially parallel to the perpendicular axis 172 and radially-outward from the de-coupler 134 to bias the control member 138 towards a protracted position as shown in FIG. 4A. Thus, without an application of a force in an opposite direction to retract the control member 138, as shown in FIG. 4B, the control member 138 is constantly disposed in the protracted position. Further, the control member biasing device 149, the passageways 141, and the head 142 of the control member 138 are sized and configured to ensure the shaft 144 never touches the stiffener biasing device 139 when the control member 138 is retracted.

During use, the stiffener 132 and the de-coupler 134 are positioned at a retracted point along the length L of the probe 110 as shown in FIG. 4B. The head 142 of the control member 138 is depressed by, e.g., a surgeon, and the shaft 144 operatively engages the de-coupler opening 150 in the de-coupler 134, and thus, the stiffener 132. Accordingly, depressing the control member 138 into the de-coupler opening 150 holds the stiffener 132 in a retracted position, beneficially withholding the force from the stiffener biasing device 139 while the control member 138 is depressed. Releasing the control member 138 pushes the control member 138 towards the protracted position and thus operatively disengages the de-coupler 134. The force from the stiffener biasing device 139 returns the stiffener 132 to the protracted position as shown in FIG. 4A.

Generally, the control member 138 may be formed of a metallic or composite material. In some embodiments, the control member 138 is formed of stainless steel, aluminum, or titanium. In other embodiments, the control member 138 is formed of a polymer composite material or ceramic composite material. The control member 138 is further discussed in FIG. 4C.

The configurations of stiffener 132, the de-coupler 134, the control member 138, and the biasing devices 139 and 149 are only exemplary and thus should not be considered limiting. Additional embodiments and configurations for different actuation mechanisms are further described below.

As shown in FIG. 4A, a nut 180 couples the stiffener 132 to the de-coupler 134. In other embodiments, the de-coupler 134 is a direct extension of the stiffener 132. That is, the de-coupler 134 and the stiffener 132 are a single, integral component. In other embodiments (e.g., as seen in FIG. 2), the de-coupler 134 and the stiffener 132 are separate components that are biased toward each other by, for example, biasing device 139. In some embodiments, the de-coupler 134 and the stiffener 132 are coupled to one another by one or more coupling mechanisms and/or adhesives. In other embodiments, the de-coupler 134 and the stiffener 132 may be snap-fit together.

Figure 4C:
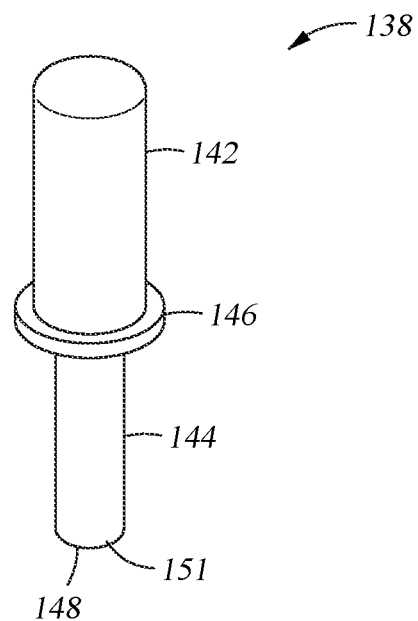
FIG. 4C illustrates a perspective view of a control member of the vitrectomy probe of FIG. 1B, according to certain embodiments of the present disclosure.

FIG. 4C illustrates a perspective view of the control member 138. As shown, the head 142 of control member 138 is an ellipse shape and the shaft 144 and flange 146 are a circular shape, but each may be a different shape such as an ellipse, circle, triangle, or rectangle. A radially-inward end 148 of the control member 138 (e.g., an end closer to the de-coupler 134) optionally includes a fillet 151 or chamfer to facilitate insertion of the shaft 144 into the de-coupler opening 150 of the de-coupler 134.

Figure 4D:
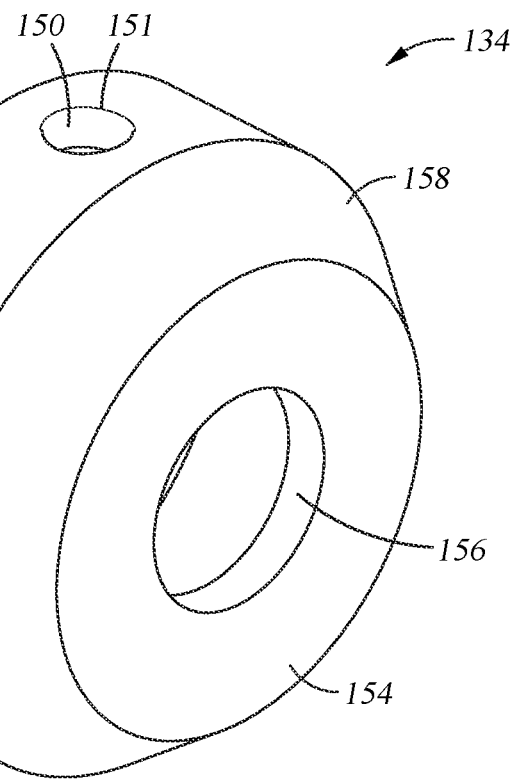
FIG. 4D illustrates a perspective view of a de-coupler of the vitrectomy probe of FIG. 1B, according to certain embodiments of the present disclosure.

FIG. 4D illustrates a perspective view of the de-coupler 134. De-coupler 134 is generally a cylindrical and hollow tube with a cap 154 and a transition (e.g., a fillet 158) between the tube and the cap 154. As shown in FIG. 4A, the distal end 131 of the stiffener 132 can be inserted through an opening 156 in the cap 154 and the cap 154 is configured to couple to the flange 136 of the stiffener 132. Thus, the de-coupler 134 and the stiffener 132 move as one piece. The de-coupler opening 150 in the de-coupler 134 optionally includes a fillet 151 or chamfer to facilitate insertion of the shaft 144 of the control member 138.

Figure 4F:
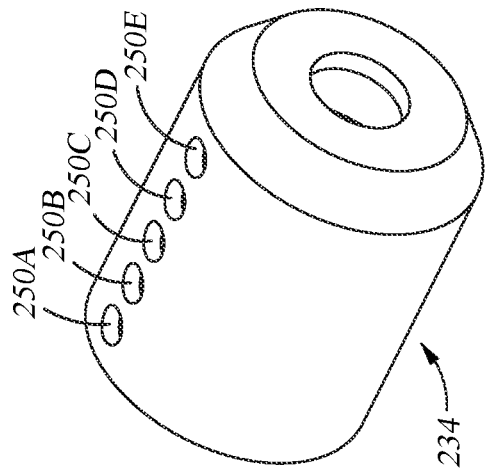
FIG. 4F illustrates a perspective view of the de-coupler of the vitrectomy probe of FIG. 4E, according to certain embodiments of the present disclosure.
Figure 4E:
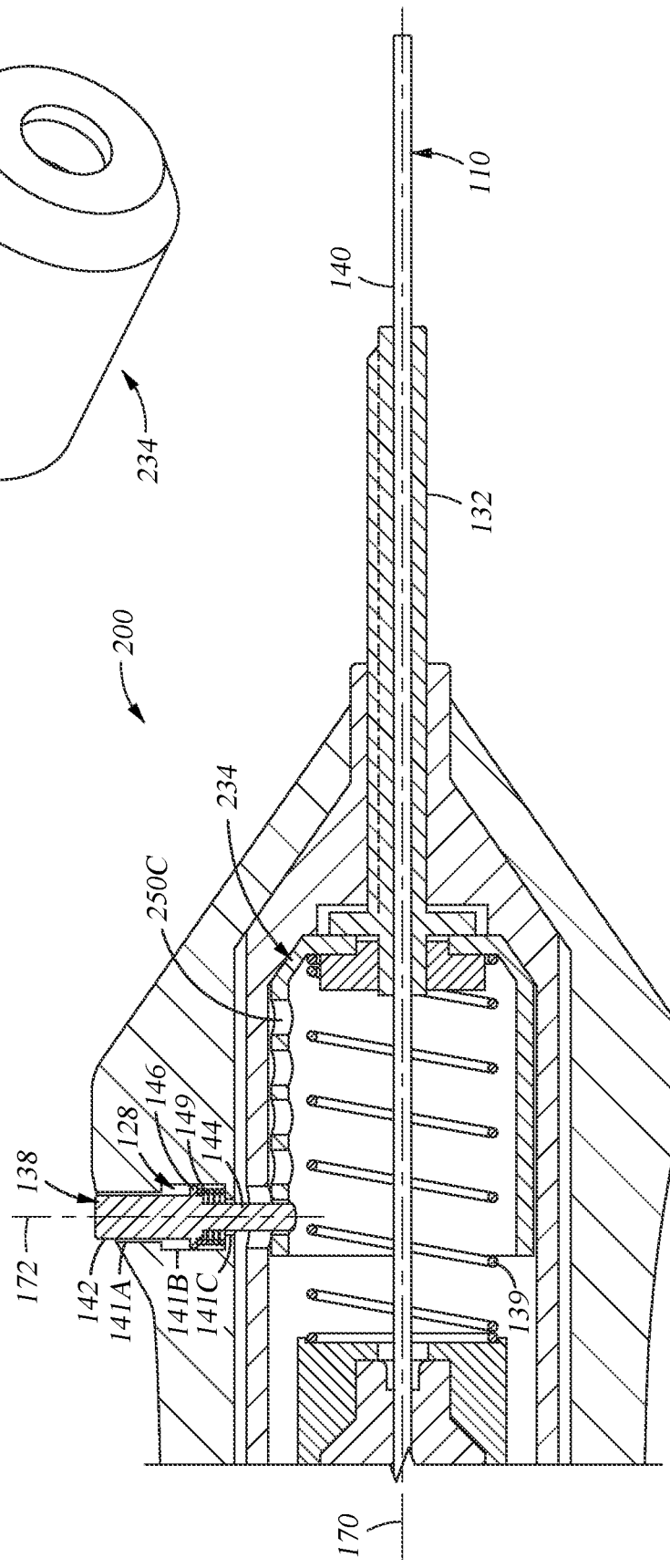
FIG. 4E illustrates a schematic cross-sectional side view of another exemplary instrument, according to certain embodiments of the present disclosure.

FIG. 4E illustrates a schematic cross-sectional side view of another exemplary instrument 200 according to certain embodiments described herein. The instrument 200 is substantially similar to the instrument 100, except for the structure of a multi-opening de-coupler 234. The de-coupler 234 is generally similar to the de-coupler 134, except the de-coupler 234 includes multiple de-coupler openings 250. The multiple de-coupler openings 250 are positioned in a straight line along the length of the de-coupler 134, as shown in FIG. 4F. The control member 138 can operationally engage any one of the de-coupler openings 250 as described in relation to FIG. 4B with respect to the de-coupler opening 150. Thus, the stiffener 132 position is adjustable relative to the probe 110, enabling a user to beneficially lock the position of the stiffener 132 (e.g., the distal end 131 of the stiffener 132) in place at different points along the length L of the probe 110.

In some embodiments, the stiffener 132 position is adjustable up to a distance of about 15 mm (millimeters) along the length L of the probe 110, such as a distance up to about 10 mm along the length L of the probe 110. For example, the stiffener 132 is adjustable up to a distance of about 5 mm along the length L of the probe 110.

FIG. 4F illustrates a perspective view of the de-coupler 234. As shown, the de-coupler openings 250 form a straight line along the length of the de-coupler 234 such that each opening (e.g., a de-coupler opening 250A) corresponds to a different stiffener position along the length L of the probe 110 as discussed in relation to FIG. 4E. The de-coupler openings 250 of the de-coupler 234 are otherwise similar to the de-coupler opening 150 of the de-coupler 134. As shown, the de-coupler 234 has four de-coupler openings 250, but other embodiments may have more or less de-coupler openings 250.

As previously discussed, in the embodiments of FIGS. 1A-4D, depressing the control member 138 of instrument 100 locks the de-coupler 134 and the stiffener 132 in place and releasing the control member 138 returns the stiffener 132 and de-coupler 134 to a protracted position. In such embodiments, the user, e.g. a surgeon, is required to hold down the control member 138 in order to lock the stiffener 132 in place, otherwise the stiffener 132 is released. However, it may be advantageous to allow the user to lock the stiffener 132 in place without requiring the user to continuously press or hold the control member 138. FIGS. 5A-5H illustrate various examples of de-couplers that can be used in conjunction with various example instruments shown in FIGS. 6A-8 to allow the user to lock the stiffener in place without having to hold the control member.

FIGS. 5A-5H illustrate perspective views of different de-couplers 334. The de-couplers 334 are generally similar to the de-couplers 134 and 234 in FIGS. 4D and 4F, respectively, except including different types or shapes of de-coupler openings 350.

Figure 5A:
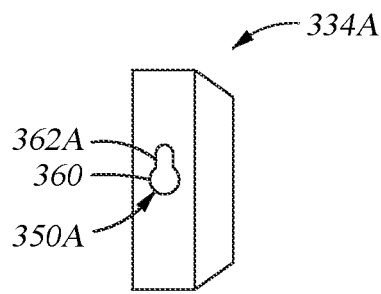
FIGS. 5A-5H illustrate perspective views of various de-couplers, according to certain embodiments of the present disclosure.

FIG. 5A shows a de-coupler 334A including a de-coupler opening 350A with a circular cutout 360 and a groove 362A. The circular cutout 360 is substantially similar to the de-coupler opening 150 in FIG. 4D. The groove 362A extends outward from the circular cutout 360 in a direction that is perpendicular to the probe longitudinal axis 170 in FIG. 4A. The groove 362A is used to operatively engage a control member (e.g., a control member 438 in FIG. 6A) and lock the de-coupler 334A in place as described in relation to FIGS. 6A-6C. This beneficially allows a user to set the position of a stiffener (e.g., a stiffener 432 in FIG. 6B) without continuously depressing the control member.

Figure 5B:
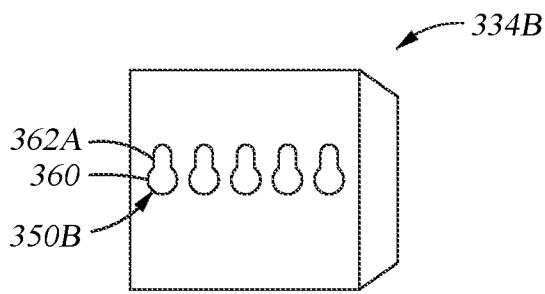

FIG. 5B shows a de-coupler 334B including multiple de-coupler openings 350B positioned in a straight line along the length of the de-coupler 334B. The de-coupler openings 350B are each substantially similar to the de-coupler opening 350A of FIG. 5A.

Figure 5C:
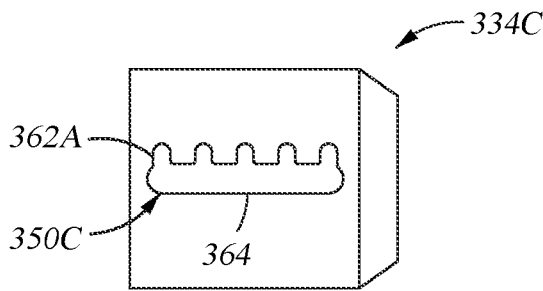

FIG. 5C shows a de-coupler 334C including a channel-shaped de-coupler opening 350C that is positioned along a straight line along the length of the de-coupler 334C. The de-coupler opening 350C includes a de-coupler channel 364 extending along the length of the de-coupler 334C and several grooves 362A. The grooves 362A extend outward from the de-coupler channel 364 in a perpendicular direction (similar to that of FIG. 5A) and are positioned at several locations along the length of the de-coupler 334C.

The de-coupler opening 350C is such that a control member can be depressed and a shaft of the control member (e.g., a shaft 444 and a control member 438 in FIG. 6A) can be inserted anywhere along the de-coupler channel 364. The de-coupler opening 250C beneficially allows a user to be less precise when operationally engaging the de-coupler 334C with the control member. The grooves 362A are used to operatively engage the control member at different positions along the de-coupler channel 364 and lock the de-coupler 334C in place as described in relation to FIG. 5A.

Figure 5D:
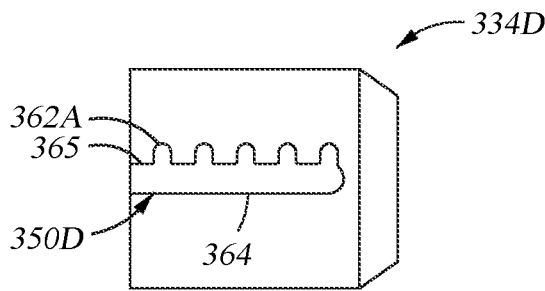
Figure 5E:
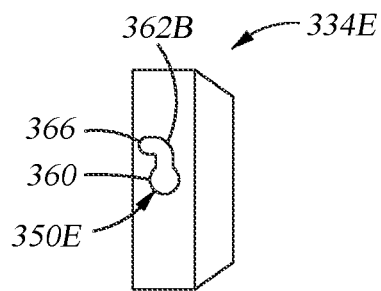
Figure 5F:
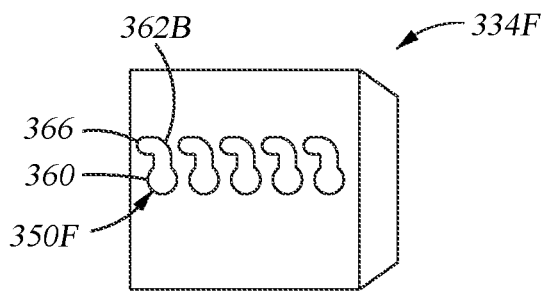

FIG. 5D shows a de-coupler 334D including a de-coupler opening 350D. The de-coupler opening 350D is generally similar to the de-coupler opening 350C of FIG. 5C, except the de-coupler channel 364 includes a channel entryway 365 at a proximal end (e.g., towards the proximal end 125 in FIG. 1B). The channel entryway 365 is a breach in the de-coupler 334D.

Note that although the de-coupler openings 350C and 350D can be used in conjunction with a control member that is configured to be depressed with the use of a biasing device (e.g., control member 138, 438, etc.), de-coupler openings 350C and 350D also allow for embodiments in which a control member (e.g., control member 638 of FIG. 8) is positioned in a depressed state at all times, such that the tip of the shaft or a notch of the shaft (e.g., notch 645 described below) is aligned (e.g., depth-wise) with and/or surrounded by the inner walls of the de-coupler opening 350D or 350C at all times. For example, in the case of de-coupler opening 350C, the tip of the shaft (or the notch) can be disposed in the de-coupler opening 350C at all times, including when the stiffener is in a protracted position as well as when the stiffener is in a retracted position. In the example of de-coupler opening 350D, even if the control member is not positioned over the de-coupler 334D when the stiffener is in a protracted position (e.g., because the de-coupler 334D may not be long enough), the shaft can slide through the channel entry way 365 as the de-coupler 334D is retracted.

FIG. 5E-5H show de-couplers 334E-H, respectively. The de-coupler openings 350E-H of FIGS. 5E-5H are generally similar to the de-coupler openings 350A-D of FIGS. 5A-5D, respectively, except for the grooves. The grooves 362B of de-couplers 334E-H differ from the grooves 362A in FIGS. 5A-5D in that the each of the grooves 362B includes a leg 366 and is generally a dogleg or L-shaped pattern. When de-couplers 334E-H are positioned in an instrument (e.g., an instrument 400 in FIGS. 6B and 6C), the leg 366 of the dogleg is parallel to the probe longitudinal axis 170 and extends towards a proximal end of the base unit 120 (e.g., towards the proximal end 125 in FIG. 1B). The leg 366 is used to operatively engage a control member (e.g., a control member 438 in FIG. 6A) when the control member is in one of the grooves 362B and lock the de-couplers 334E-H in place. The leg 366 ensures the de-couplers 334E-H do not rotate when locked in place as described in relation to FIGS. 6B and 6C.

Figure 7A:
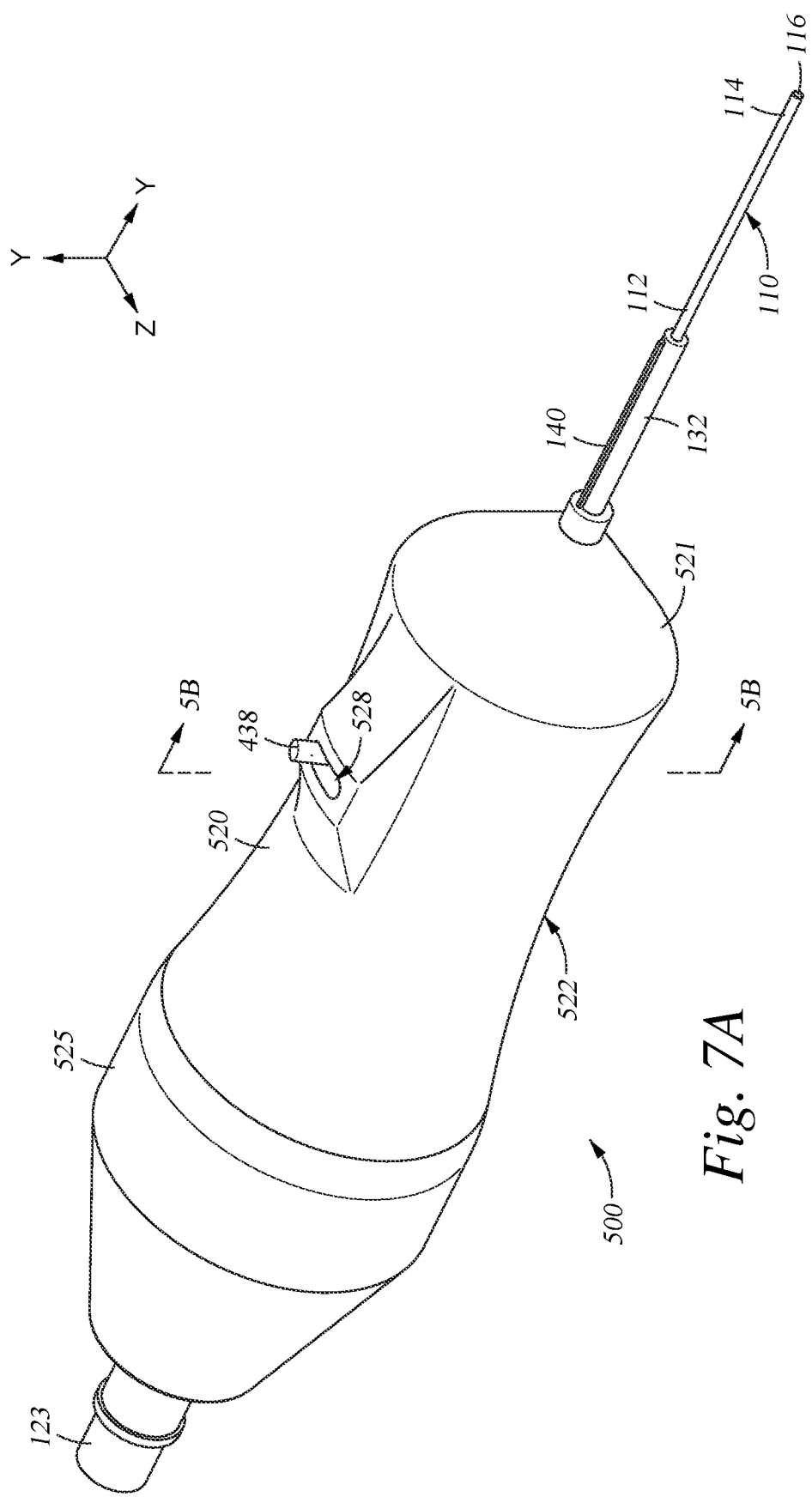
FIG. 7A illustrates a perspective view of another exemplary instrument, according to certain embodiments of the present disclosure.

The de-couplers 334A-H described in relation to FIGS. 5A-5H can be used in several different instruments. FIGS. 6A-6C show how a stiffener 432 can be rotated to engage a control member 438 using the grooves 362A and 362B shown in FIGS. 5A-5H. FIGS. 7A-8 show how the control member 438 can slide to engage the grooves 362A and 362B.

FIGS. 6A-6C illustrate different features and views of another exemplary instrument 400, which is generally similar to exemplary instrument 100 in FIGS. 1-4B. The instrument 400 includes a control member 438, a stiffener 432, and the de-coupler 334A from FIG. 5A. The control member 438 is generally similar to the control member 138, except for having a notch, and is described in relation to FIG. 6A. The stiffener 432 is substantially similar to the stiffener 132, except the stiffener 432 does not include the keying feature 140. Thus, the stiffener 432 and the de-coupler 334A are free to collectively rotate about the probe longitudinal axis (e.g., the probe longitudinal axis 170 shown in FIG. 4A) of the probe 110.

FIG. 6A illustrates a perspective view of the control member 438. As shown, the control member 438 includes a head 142, a flange 146, and a shaft 444. The shaft 444 is substantially similar to the shaft 144 in FIG. 4C, except the shaft 444 includes a notch 445 near the radially-inward end 148 of the control member 438. The notch 445 operatively engages the groove 362A in the de-coupler 334A, as described in relation to FIGS. 6B and 6C.

FIGS. 6B and 6C illustrate schematic cross-sectional views of the exemplary instrument 400 from a viewpoint at a distal end of the instrument 400. The stiffener biasing device 139 is omitted to better illustrate the locking mechanism of the control member 438 and the de-coupler 334A. As previously discussed, the stiffener 432 and the de-coupler 334A are free to rotate together about the probe longitudinal axis 170. As shown in FIG. 6B, the control member 438 is depressed and the shaft 444 of the control member 438 is inserted into the circular cutout 360 of the de-coupler opening 350A such that the notch 445 aligns with the groove 362A in the de-coupler 334A. As shown in FIG. 6C, the stiffener 432 and thus the de-coupler 334A rotate clockwise 476 and the notch 445 operatively engages the groove 362A. The stiffener 432 can be rotated relative to the probe 110 or the base unit 120 of the instrument 100 manually by a surgeon. For example, the notch 445 fits inside the groove 362A and overhangs the de-coupler 334A, guiding the notch 445 into the groove 362A as the stiffener 432 and de-coupler 334A are rotated. The control member 438 is then released and the control member biasing device 149 pushes the control member 438 in a radially-outward direction from the de-coupler 334A such that the notch 445 pushes against the de-coupler 334A and the control member 438 locks the de-coupler 334A and, thereby, the stiffener 432 in place. To release the de-coupler 334A, the surgeon can rotate the stiffener 432 counter-clockwise, thereby moving the notch 445 out of the groove 362A. The control member 438 is released and the stiffener biasing device 139 pushes the stiffener to the protracted position as shown in FIG. 4A.

In other embodiments not shown, the de-coupler (e.g., the de-coupler 334E in FIG. 5E) has a groove 362B with a leg 366. Once the notch 445 operationally engages the groove 362B and the de-coupler 334E is rotated as far clockwise 476 as possible, the stiffener biasing device 139 pushes the de-coupler in the distal direction (e.g., towards the distal end 121 in FIG. 1B) and the notch 445 operationally engages the leg 366 of the groove 362B, beneficially preventing rotation and also locking the de-coupler 334E and the stiffener 432 in place. To release the de-coupler 334E, the stiffener 432 is pushed in a proximal direction (e.g., towards the proximal end 125 in FIG. 1B) against the force of the stiffener biasing device 139 and rotated counter-clockwise. This moves the notch 445 out of the leg 366 and the groove 362B. The control member 438 is released and the stiffener biasing device 139 pushes the stiffener to the protracted position as shown in FIG. 4A.

FIG. 7A illustrates a perspective view of an exemplary instrument 500 according to certain embodiments described herein. The instrument 500 is generally similar to instruments 100 and 400 in FIGS. 1B and 6B-C, respectively, except as discussed herein. In particular, the instrument 500 uses the control member 438 to push radially-inward towards a de-coupler (e.g., the de-coupler 334A in FIG. 7B) and slide to lock the de-coupler and the stiffener 132 in position. The instrument 500 includes a base unit 520 that has a cutout 528 and an outer surface 522. The cutout may be referred to as a base unit channel that is different from the de-coupler channel of the de-coupler. The control member 438 is partially disposed inside the cutout 528. The base unit 520 and the outer surface 522 are substantially similar to the base unit 120 and the outer surface 522 in FIG. 1B, except for the differences from the cutout 528. The base unit 520 includes a distal end 521 and a proximal end 525.

Figure 7B:
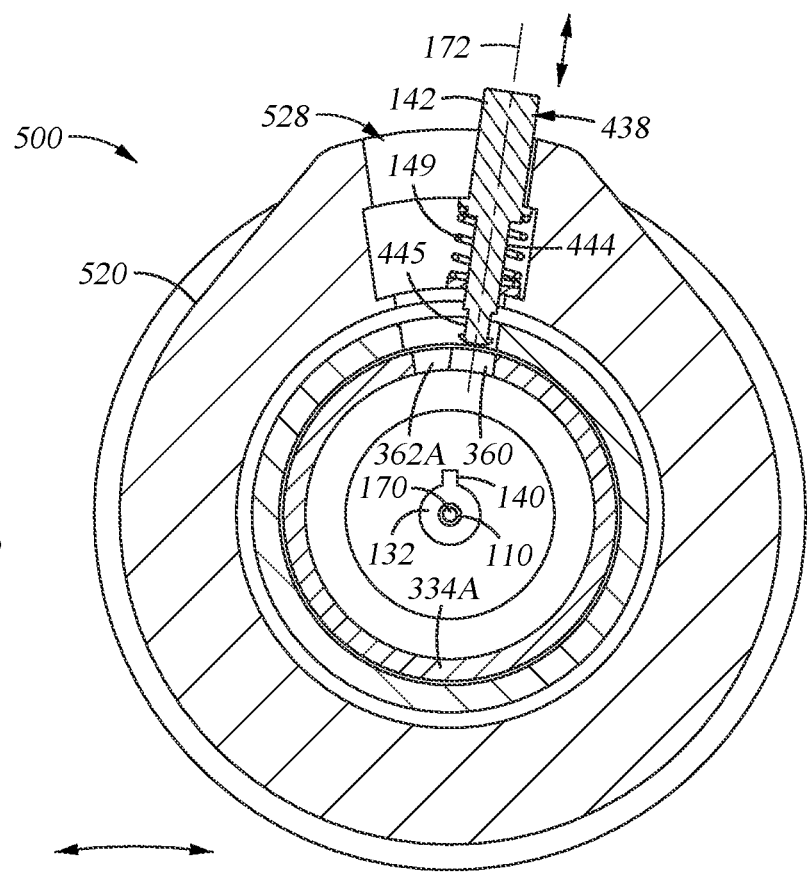
FIGS. 7B-7C illustrate a schematic front cross-sectional view of the instrument of FIG. 7A, according to certain embodiments of the present disclosure.
Figure 7C:
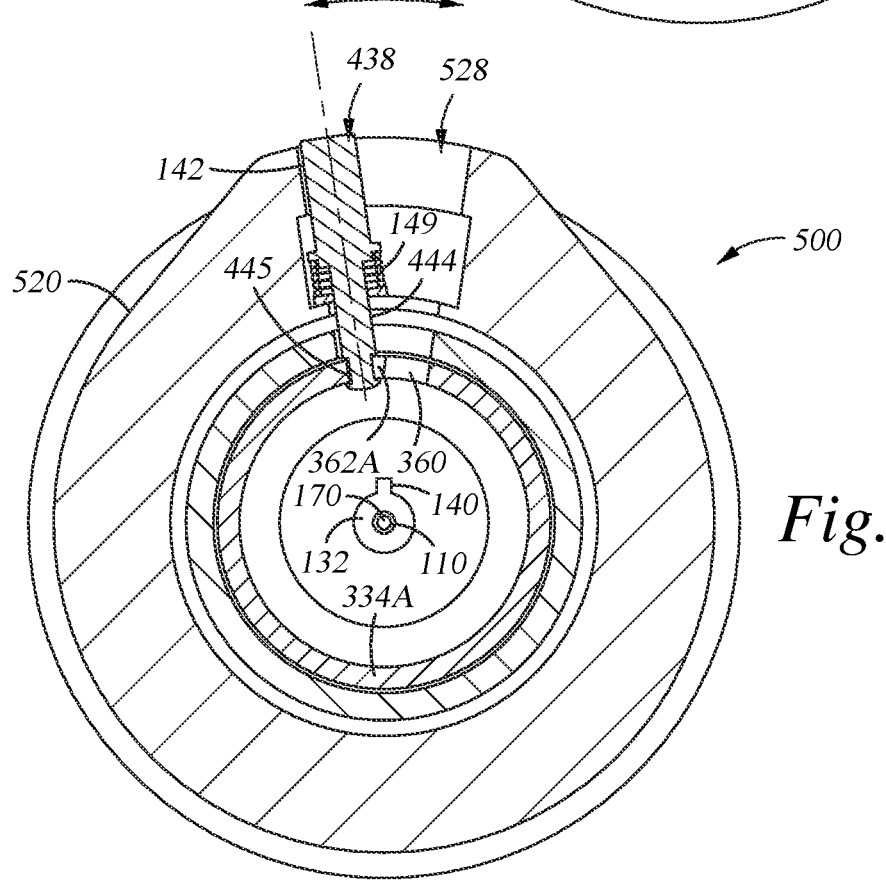
Figure 8:
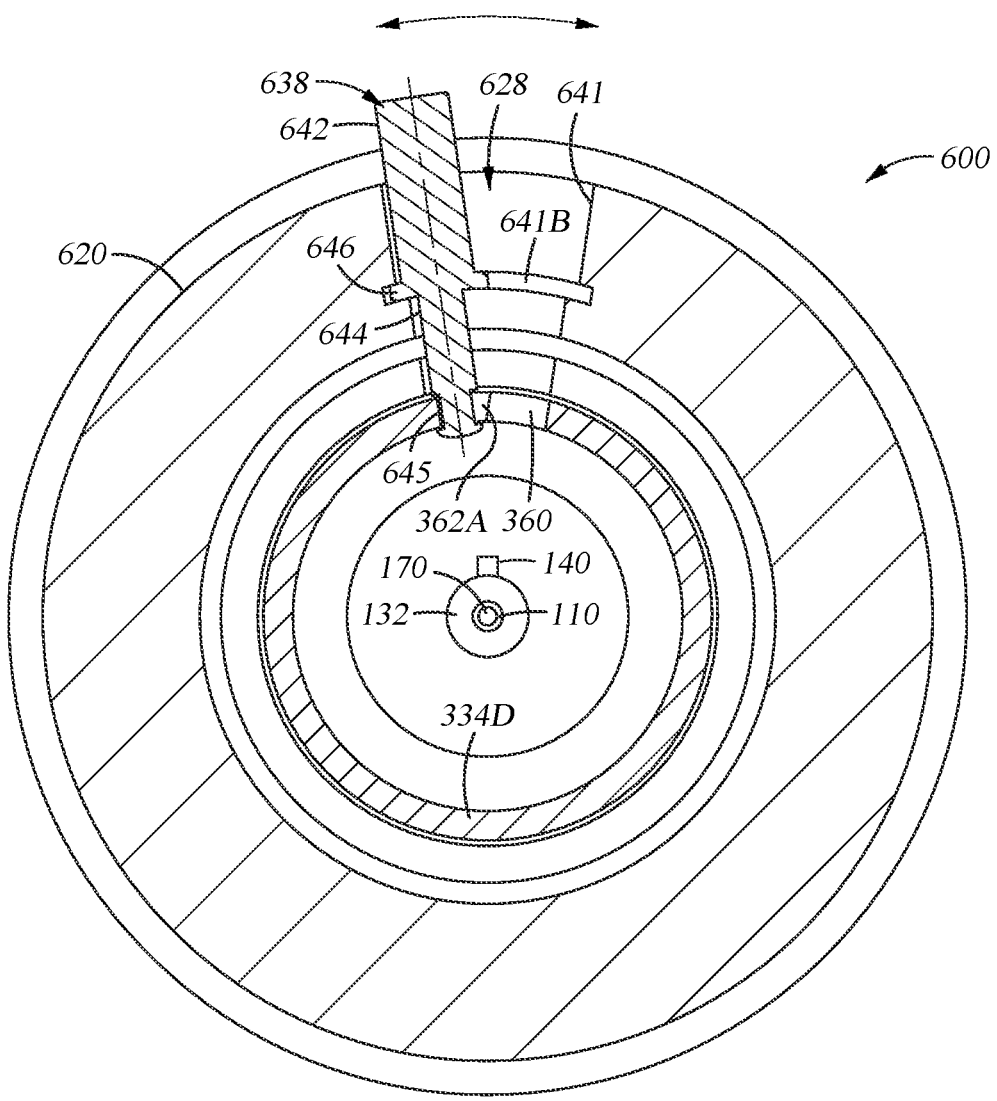
FIG. 8 illustrates a schematic front cross-sectional view of another exemplary instrument, according to certain embodiments of the present disclosure.

FIGS. 7B and 7C illustrate schematic cross-sectional views of the instrument 500. Instrument 500 uses the stiffener 132 that was described in relation to FIGS. 1A-4B. As previously discussed in FIGS. 4A and 4B, the stiffener 132 is constrained from rotation about the probe longitudinal axis 170 by the keying feature 140. Thus, the de-coupler 334A is constrained from rotating. The stiffener biasing device 139 is omitted to better illustrate the locking mechanism of the control member 438 and the de-coupler 334A.

The cutout 528 is configured to allow bidirectional pushing of the control member 438 along the perpendicular axis 172, similar to what was previously described in relation to FIGS. 4A and 4B. The cutout 528 is further configured to allow sliding of the control member 438 about the probe longitudinal axis 170. As shown in FIG. 7B, the control member 438 is depressed along the perpendicular axis 172 and the shaft 444 of the control member 438 is inserted into the circular cutout 360 of the de-coupler 334A such that the notch 445 aligns with the groove 362A in the de-coupler 334A. As shown in FIG. 7C, the control member 438 and the notch 445 slide about the probe longitudinal axis 170 and the notch 445 operatively engages the groove 362A. The control member 438 locks the de-coupler 334A and the stiffener 432 in place similar to what was described in relation to FIGS. 6B and 6C. To release the de-coupler 334A, the control member 438 slides in an opposite direction to move the notch 445 out of the groove 362A. The control member 438 is released and the stiffener biasing device 139 pushes the stiffener 132 to the protracted position as shown in FIG. 4A.

As described above, although previous FIGS. 1A-4F and 6A-7C discussed depressing a control member to insert the shaft into an opening of a de-coupler, in certain other embodiments (shown in FIG. 8) the control member's shaft may slide through or be positioned within a channel-shaped de-coupler opening of the de-couplers shown in FIG. 5C, 5D, 5G, or 5H without the control member having to be depressed. In such embodiments, to lock the stiffener in place, the user can slide control member, for example, about the probe longitudinal axis 170, as further described in relation to FIG. 8.

FIG. 8 illustrates a schematic cross-sectional view of an exemplary instrument 600. The cross-sectional view is substantially similar to the cross-sectional view of FIGS. 7B and 7C. The instrument 600 is generally similar to the instrument 500 in FIGS. 7B and 7C, except as discussed herein. In particular, the instrument 600 uses the control member 638 to slide to lock the stiffener 132 in position. The control member 638 includes a head 642, a flange 646, and a shaft 644. The shaft 644 includes a notch 645. The stiffener biasing device 139 is omitted to better illustrate the locking mechanism of the control member 638 and the de-coupler 334D (or de-coupler 334H)

The instrument 600 includes a base unit 620 having a cutout 628. The cutout 628 may be referred to as a base unit channel that is different from the de-coupler channel of the de-coupler. The cutout 628 includes multiple-sized passageways 641 similar to the passageways 141 discussed in FIGS. 4A and 4B, except a second passageway 641B conforms to the flange 646 of the control member 638. The flange 646 operatively engages the second passageway 641B, which guides the flange 646 and thus the control member 638 through the cutout 628 about the probe longitudinal axis 170 when the control member 638 is slidably actuated by the user. Thus, the second passageway 641B is configured to be a guide channel to guide the control member 638 when actuated by the user and may be referred to as a guide channel. As shown, the second passageway 641B is a curved channel that is curved about the probe longitudinal axis 170.

The de-coupler 334D, as previously discussed in FIG. 5D, includes the de-coupler channel 364 and the channel entryway 365. The stiffener 132 travels along the length L of the probe 110. As the stiffener 132 travels towards the proximal end 525 of the base unit 620, the channel entryway 365 and the de-coupler channel 364 of the de-coupler 334D operatively engage the notch 645 of the control member 638. As shown, when the shaft 644 and the notch 645 align with one of grooves 362A, the control member 638 can be slid about the probe longitudinal axis 170 and into one of the grooves 362A, causing the notch 645 to operatively engage the groove. Therefore, the control member 638 locks the de-coupler 334D and the stiffener 132 in place similar to as described in relation to FIGS. 7B and 7C. To release the de-coupler 334D, the control member 638 slides in an opposite direction to move the notch 645 out of the groove 362A and the stiffener biasing device 139 pushes the stiffener 132 to the protracted position as shown in FIG. 4A.

Figure 5G:
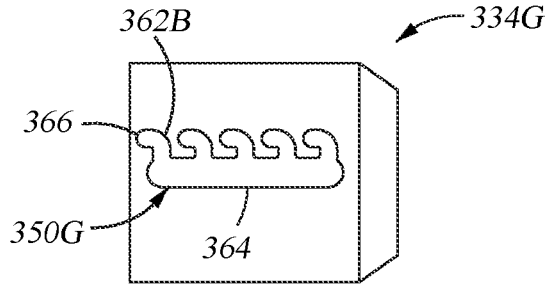
Figure 5H:
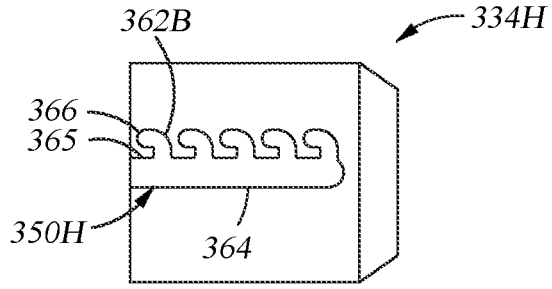

In certain embodiments, the sliding-only locking mechanism of the instrument 600 is compatible with de-couplers 334C and 334G of FIGS. 5C and 5G, respectively. For example, in relation to the de-coupler 334C, the shaft 444 of the control member 438 is disposed in the de-coupler channel 364 at all times while the stiffener 132 travels along the length L of the probe 110. When locking the de-coupler 334C in place, the notch 445 of the control member 438 operationally engages one of the grooves 362A of the de-coupler 334C as previously described with respect to the de-coupler 334D. The de-coupler 334G may be used in a similar manner. In such embodiments, a stiffener without a keying feature (e.g., the stiffener 432) may be used because the control member is always disposed inside an opening of the de-coupler.

In another embodiment, the cutout 628 comprises a track with substantially planar surfaces, perpendicular to the probe longitudinal axis 170 and the perpendicular axis 172, upon which a control member may slidably and dynamically be actuated by the user. The planar surfaces of the track provide a flat surface for a control member (e.g., the control member 638) to traverse. In such embodiments, the second passageway 641B is a linear channel that is straight along the track.

FIG. 9A illustrates a perspective view of an exemplary instrument 700 according to certain embodiments described herein. Although instrument 700 is generally similar to the instrument 100 from FIG. 4A, the configuration of instrument 700 may be applied to any of the instruments discussed herein.

As shown, the instrument 700 comprises a probe 710 and a base unit 720 having a distal end 721. The base unit 720 includes an interior chamber 724 and a base unit opening 717. A stiffener 732 surrounds the probe 710. The stiffener 732 and the probe 710 are disposed in the interior chamber 724 and through the base unit opening 717 of a distal end 721 of the base unit 720. The stiffener 732 includes a keying feature 740 which operationally engages the base unit opening 717 to prevent the stiffener 732 from rotating.

A cutout 728 is formed in the base unit 720 and a control member 738 is partially disposed in a cutout 728. The control member 738 includes a control member biasing device 749. The control member biasing device 749 includes several extensions as described in relation to FIG. 9B. The cutout 728 includes multiple-sized passageways 741 configured to accommodate the control member 738 and the control member biasing device 749. For example, a passageway 741B is formed to accommodate a deflection of the control member biasing device 749 when the control member 738 is depressed radially-inward towards the de-coupler 734. The passageways 741A and 741C are similarly formed to accommodate other parts of the control member 738.

A de-coupler 734 is coupled to the stiffener 732 and a biasing device 739 applies a biasing force against the de-coupler 134. The biasing force pushes the de-coupler 734 and the stiffener 732 in a distal direction (e.g., towards the distal end 721) to a protracted position as shown in FIG. 9A. When the stiffener 732 and the de-coupler 734 are retracted in a direction opposite the distal direction (e.g., a proximal direction), the control member 738 may be depressed to engage the de-coupler 734 and lock the stiffener 732 in position as similarly described in FIGS. 4A and 4B.

FIG. 9B illustrates a perspective view of the control member 738. As shown, the control member 738 includes a head 742 and a shaft 744 disposed at opposite ends of the control member 738. A flange 746 is disposed between the head 742 and the shaft 744. The flange 746 includes several extensions 747 that comprise the control member biasing device 749. The extensions 747 extend in a direction towards and radially outward from the shaft 744. Thus, as shown, the control member biasing device 749 and the control member 738 are a single, integral component, beneficially reducing the total components in instrument 700. In certain embodiments, the extensions 747 are made from a flexible but stiff material such as polypropylene, polycarbonate, acrylonitrile butadiene styrene, and the like. When the control member 738 is depressed, the extensions 747 contact the passageway 741B and the force depressing the control member 738 deforms the extensions 747 as the shaft 744 travels towards the de-coupler 734. When the force is removed, the extensions 747 return to their un-deformed shape. Thus, the extensions 747 function as a spring.

In summary, embodiments of the present disclosure include structures and mechanisms for adjusting the stiffness of microsurgical instruments, such as small-gauge instruments for minimally-invasive ophthalmologic operations. The instruments described above include embodiments wherein a user, such as a surgeon, may adjust the stiffness of the instruments during use thereof. Accordingly, the described embodiments enable a surgeon to access a wider range of tissues with a single instrument, thus expanding the applicability of smaller gauge instruments to a greater range of indications.

Certain embodiments described herein enable a surgeon to dynamically adjust the stiffness and length of a vitrectomy probe to access all areas of a vitreous cavity during a single procedure. The adjustment of the probe may be carried out prior to insertion of the probe into the eye or after the probe has already been inserted therein. Thus, the described embodiments may be utilized to facilitate access to the posterior segment of an eye during vitreous surgeries while retaining the benefits of smaller gauge probes, such as increased patient comfort, less conjunctival scarring, less postoperative inflammation, and faster healing time. Although vitreous surgery is discussed as an example of a surgical procedure that may benefit from the described embodiments, the advantages of an instrument with adjustable stiffness may benefit other surgical procedures as well.

While the foregoing is directed to embodiments of the present disclosure, other and further embodiments of the disclosure may be devised without departing from the basic scope thereof, and the scope thereof is determined by the claims that follow.

Additional Considerations

The preceding description is provided to enable any person skilled in the art to practice the various embodiments described herein. The examples described herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A surgical instrument, comprising:
a base unit, the base unit configured to be held by a user;
a probe disposed through a base unit opening in a distal end of the base unit, the probe having a length parallel to a probe longitudinal axis thereof;
a stiffener disposed through the base unit opening in the base unit, the stiffener formed of a hollow tubular member slidably coupled to and surrounding at least a portion of the probe; and
an actuation mechanism configured to extend the stiffener along the length of the probe in a distal direction, wherein the actuation mechanism comprises:
a first biasing device,
a de-coupler comprising a de-coupler proximal surface and a de-coupler distal surface, wherein the de-coupler proximal surface is configured to contact the first biasing device, and
an annular flange integral with or affixed to the stiffener, wherein the annular flange comprises an annular flange proximal surface and an annular flange distal surface,
wherein the first biasing device is configured to apply a first biasing force against the de-coupler proximal surface to push the de-coupler distal surface against the annular flange proximal surface which pushes, the annular flange distal surface toward an interior surface of the base unit.

2. The surgical instrument of claim 1, further comprising:
a control member configured to lock the stiffener in position;
wherein the de-coupler is configured to interact with the control member.

3. The surgical instrument of claim 2, wherein the de-coupler comprises a de-coupler opening.

4. The surgical instrument of claim 3, wherein the de-coupler opening comprises one or more through holes or a de-coupler channel.

5. The surgical instrument of claim 1, wherein the annular flange distal surface contacts the interior surface of the base unit when the stiffener is in a fully extended position on the probe.

6. A surgical instrument, comprising:
a base unit, the base unit configured to be held by a user;
a probe disposed through a base unit opening in a distal end of the base unit, the probe having a length parallel to a probe longitudinal axis thereof;
a stiffener disposed through the base unit opening in the base unit, the stiffener formed of a hollow tubular member slidably coupled to and surrounding at least a portion of the probe; and
an actuation mechanism configured to extend the stiffener along the length of the probe in a distal direction, wherein the actuation mechanism comprises:
a first biasing device,
a de-coupler, and
an annular flange integral with or affixed to the stiffener,
wherein the first biasing device is configured to apply a first biasing force, through the de-coupler, against the annular flange of the stiffener in the distal direction; and
a control member configured to lock the stiffener in position;
wherein the de-coupler is configured to interact with the control member;
wherein the de-coupler comprises a de-coupler opening;
wherein the de-coupler opening comprises one or more through holes or a de-coupler channel;
wherein the de-coupler opening comprises one or more through holes or a de-coupler channel;
wherein the control member comprises a protrusion configured to operatively engage the de-coupler opening of the de-coupler to lock the stiffener in position, the control member and the protrusion having a control member longitudinal axis perpendicular to the probe longitudinal axis of the probe.

7. The surgical instrument of claim 6, wherein the control member is partially disposed within a base unit channel formed in the base unit and the base unit channel is formed along the control member longitudinal axis.

8. The surgical instrument of claim 7, wherein pushing the control member along the base unit channel operatively engages the one or more through holes of the de-coupler.

9. The surgical instrument of claim 7, wherein the control member further comprises a control member biasing device, and wherein the control member biasing device is:
disposed in the base unit channel formed in the base unit, and
configured to apply a control member biasing force against the control member in a direction radially-outward from the de-coupler.

10. The surgical instrument of claim 9, wherein:
the control member further comprises a flange,
the control member biasing device is a spring, and
the control member biasing force is applied against the flange of the control member.

11. The surgical instrument of claim 7, wherein the de-coupler opening of the de-coupler further comprises a groove extending in a direction that is perpendicular to the probe longitudinal axis of the probe.

12. The surgical instrument of claim 11, wherein the protrusion of the control member comprises a shaft with a notch configured to operatively engage the de-coupler opening of the de-coupler.

13. The surgical instrument of claim 12, wherein
the de-coupler is configured to move about the probe longitudinal axis of the probe when rotated about the probe longitudinal axis,
the notch of the control member is configured to operatively engage the groove of the de-coupler when the stiffener is rotated in a first direction, and
the notch of the control member is configured to operatively disengage the groove of the de-coupler when the stiffener is rotated in a second direction.

14. The surgical instrument of claim 12, wherein:
the control member is partially disposed within a guide channel formed in the base unit and the guide channel is formed about the probe longitudinal axis of the probe,
the control member is configured to move about the probe longitudinal axis when slid along the guide channel,
the notch of the control member is configured to operatively engage the groove of the de-coupler when the control member is slid in a first direction, and
the notch of the control member is configured to operatively disengage the groove of the de-coupler when the control member is slid in a second direction.

15. The surgical instrument of claim 14, wherein the guide channel is a linear channel or a curved channel.

16. A surgical instrument, comprising:
- a base unit, the base unit configured to be held by a user;
- a probe disposed through a base unit opening in a distal end of the base unit, the probe having a length parallel to a probe longitudinal axis thereof;
- a stiffener disposed through the base unit opening in the base unit, the stiffener formed of a hollow tubular member slidably coupled to and surrounding at least a portion of the probe; and
- an actuation mechanism configured to extend the stiffener along the length of the probe in a distal direction, wherein the actuation mechanism comprises:
  - a first biasing device,
  - a de-coupler, and
  - an annular flange integral with or affixed to the stiffener, wherein the first biasing device is configured to apply a first biasing force, through the de-coupler, against the annular flange of the stiffener in the distal direction;

wherein:
- the stiffener further comprises a keying feature; and
- the base unit opening in the distal end of the base unit is configured to operatively engage the keying feature to prevent rotation of the stiffener.

* * * * *